United States Patent
Kumar et al.

(10) Patent No.: US 8,308,726 B2
(45) Date of Patent: Nov. 13, 2012

(54) ELECTROMAGNETICALLY CONTROLLED TISSUE CAVITY DISTENDING SYSTEM

(76) Inventors: Atul Kumar, Jaipur (IN); Alka Kumar, Jaipur (IN)

(*) Notice: Subject to any disclaimer, the term of this patent is extended or adjusted under 35 U.S.C. 154(b) by 1297 days.

(21) Appl. No.: 11/216,170

(22) Filed: Sep. 1, 2005

(65) Prior Publication Data

US 2006/0052666 A1 Mar. 9, 2006

(30) Foreign Application Priority Data

Sep. 3, 2004 (IN) .......................... 1674/DEL/2004

(51) Int. Cl.
*A61M 31/00* (2006.01)

(52) U.S. Cl. .............. 606/67; 604/32; 604/33; 604/34; 604/70; 604/152; 604/264; 604/331; 604/355; 604/541; 604/218; 604/219; 604/220; 604/221; 604/222; 604/223; 604/224; 604/225; 604/226; 604/227; 604/228; 604/229; 604/230; 604/231; 604/890.1; 604/892.1; 604/118; 604/119; 604/120; 604/121; 604/151; 604/153; 604/154; 604/155; 604/134; 604/135; 604/136; 604/137; 604/139; 604/246; 604/247; 604/248; 604/249; 604/250; 604/251; 604/252; 604/253; 604/254; 604/255; 604/256; 606/200; 600/431; 600/432; 600/433; 600/434; 600/435

(58) Field of Classification Search .............. 604/32–34, 604/70, 264, 331, 355, 541, 218–231, 890.1, 604/892.1, 118–121, 151–155, 134–139, 604/246–256; 606/200; 600/431–435
See application file for complete search history.

(56) References Cited

U.S. PATENT DOCUMENTS

| 2,689,565 A | * | 9/1954 | Gobel .............................. 604/34 |
| 3,051,173 A | * | 8/1962 | Johnson et al. ............... 604/152 |
| 3,214,067 A | * | 10/1965 | Linington ..................... 222/341 |
| 3,812,855 A | * | 5/1974 | Banko .............................. 604/31 |
| 4,294,251 A | | 10/1981 | Greenwald et al. |
| 4,650,461 A | * | 3/1987 | Woods ............................ 604/28 |
| 4,831,988 A | * | 5/1989 | Hoefken et al. ............. 123/501 |
| 4,902,277 A | | 2/1990 | Mathies et al. |
| 4,921,477 A | * | 5/1990 | Davis .............................. 604/22 |
| 4,941,872 A | | 7/1990 | Felix et al. |

(Continued)

OTHER PUBLICATIONS

F. Loffer, et al., "Hysteroscopic Fluid Monitoring Guidelines", *Journal of the American Assoc. of Gynecologic Laparoscopists*, Nov. 10, 1999.

*Primary Examiner* — Nicholas Lucchesi
*Assistant Examiner* — Scott Medway
(74) *Attorney, Agent, or Firm* — Dickstein Shapiro LLP

(57) ABSTRACT

A system to minimize fluid turbulence inside a tissue cavity during endoscopic procedures. A body tissue cavity of a subject is distended by continuous flow irrigation using a solenoid operated pump on the inflow side and a positive displacement pump, such as a peristaltic pump, on the outflow side, such that the amplitude of the pressure pulsations created by the outflow positive displacement pump inside the said tissue cavity is substantially dampened to almost negligible levels. The present invention also provides a method for accurately determining the rate of fluid loss into the subject's body system during any endoscopic procedure without utilizing any deficit weight or fluid volume calculation, the same being accomplished by using two fluid flow rate sensors. The present invention also provides a system of creating and maintaining any desired pressure in a body tissue cavity for any desired cavity outflow rate.

40 Claims, 8 Drawing Sheets

U.S. PATENT DOCUMENTS

| | | | |
|---|---|---|---|
| 5,322,417 A * | 6/1994 | Ottinger et al. | 417/50 |
| 5,346,508 A * | 9/1994 | Hastings | 607/99 |
| 5,420,470 A * | 5/1995 | Fanning et al. | 310/71 |
| 5,496,267 A * | 3/1996 | Drasler et al. | 604/22 |
| 5,520,638 A | 5/1996 | O'Quinn et al. | |
| 5,578,012 A | 11/1996 | Kamen et al. | |
| 6,364,637 B1 * | 4/2002 | Hase et al. | 417/413.1 |
| 6,569,147 B1 * | 5/2003 | Evans et al. | 604/509 |
| 2005/0209507 A1 * | 9/2005 | Suzuki et al. | 600/133 |

\* cited by examiner

ELECTROMAGNETICALLY CONTROLLED TISSUE CAVITY DISTENDING SYSTEM

FIELD OF INVENTION

The present invention relates to a system for distending body tissue cavities of subjects utilizing continuous flow irrigation during endoscopic procedures. The system and the methods of the present invention described above can be used in any endoscopic procedure requiring continuous flow irrigation few examples of such endoscopic procedures being hysteroscopic surgery, arthroscopic surgery, trans uretheral surgery (TURP), endoscopic surgery of the brain and endoscopic surgery of the spine. The proposed invention can also have certain useful non medical applications.

BACKGROUND OF THE INVENTION

Endoscopic surgery is becoming increasingly popular because of the following reasons:
(a) it is a minimally invasive form of surgery,
(b) it avoids large incisions over the skin and muscle,
(c) it is associated with less pain,
(d) there is a relatively less requirement of blood transfusions and
(e) the patients can return back to normal work relatively early with minimal loss of working days.

While in the corresponding open conventional surgeries a relatively large body part consisting of skin and muscle needs to be cut in order to gain access to an underlying body tissue cavity, in endoscopic surgery instead of cutting body structures like skin and muscle an endoscope is introduced into the body cavity via the natural opening of a cavity, if such exists, or alternatively a minute hole is made in the wall of the cavity through which the endoscope is introduced to visualize the interior of the body tissue cavity and to perform major or minor endoscopic surgical procedures. For this reason endoscopic surgery is also sometimes called 'key hole' or 'minimal access surgery'. Besides reducing the pain associated with surgery, endoscopic surgery also helps in reducing the medical expenses.

Endoscopic Surgery is Primarily Related to a Tissue Cavity

All endoscopic surgeries are carried out on a existing body cavity which is distended or 'ballooned up' by a suitable distending apparatus which permits the inner lining of the said tissue cavity to be visualized by the help of an endoscope. Though multiple endoscopic procedures have become established as the preferred surgical modality but still there is immense scope of increasing the safety and efficiency of the such existing endoscopic procedures by improving upon the existing techniques and apparatus used for distending body tissue cavities. Hysteroscopy, arthroscopy, TURP (transuretheral resection of the prostate), endoscopic surgery of the brain and endoscopic surgery of the spine are few of the routinely performed endoscopic procedures and the organs related to such surgeries being uterus, human joints, bladder, brain and the spine respectively. The list of endoscopic surgeries is long, ever increasing and there is hardly any body organ or organ system to which the benefits of endoscopy have not been extended.

Tissue Cavity is Initially Collapsed in its Natural State

In the natural state tissue cavities are collapsed structures and the cavity walls are in apposition with each other as if kissing each other. Thus if an endoscope is introduced in such a collapsed cavity no endoscopic visualization is possible unless the cavity is ballooned up by filling it with a transparent fluid or a gas. Such ballooning of a tissue cavity is technically termed as 'cavity distension'. No endoscopic procedure can be performed without an efficient cavity distending system and no endoscopic procedure should be attempted without a safe distending system because unsafe tissue cavity distending means can lead to extreme human morbidity and even the death of a patient and such grim realities shall be discussed in the later sections of this manuscript. Cavity distension provides both endoscopic visualization and mechanical distension which is necessary for the movement of endoscopic instruments.

Continuous Flow Irrigation

In the present invention, the Inventors are focused on a system for distending body tissue cavities for those endoscopic procedures in which the cavity needs to be distended by utilizing continuous flow irrigation only. Here, the term 'continuous flow irrigation' means that fluid simultaneously enters and escapes from a tissue cavity via separate entry and exit points, as a result of which a positive fluid pressure is created inside the tissue cavity which distends the cavity.

The Need for Continuous Flow Irrigation

Any tissue cavity can be easily distended in a 'static manner' by simply pushing fluid via a single inflow tube inserted into the cavity and in this manner a desired cavity pressure can be developed and also maintained. For example, a cavity can be distended by pressing on the piston of a simple syringe filled with fluid with the outlet end of the syringe being connected to the cavity by a tube. Alternatively a fluid filled bottle may be elevated to a suitable height and under the influence of gravity fluid from such bottle may be allowed to enter the cavity via a tube connecting the said bottle to the cavity and in this manner a desired static pressure can be developed and also maintained. Though it is very easy to achieve distension by the said static manner, it is not a practical solution because blood and tissue debris which are invariably released from the fragile cavity inner lining mix with the distending fluid and endoscopic vision gets clouded within a few seconds or a few minutes. Thus continuous flow irrigation is needed to constantly wash away blood and tissue debris in order to maintain constant clear endoscopic vision.

Cavity Pressure and Cavity Flow Rate

It is obvious that cavity fluid pressure and the flow rate through the cavity are the two basic parameters associated with all continuous flow irrigation systems.

An Efficient Distending System

The Inventors believe that an efficient distending system is the one which provides a predictably continuous clear visualization and a predictably stable mechanical stabilization of the cavity walls. In order to achieve this the Inventors believe that a suitable stable constant precise cavity pressure and a suitable stable precise cavity flow rate have to be created and maintained in a predictable and controlled manner. The cavity pressure should be adequate so that vision is not clouded by oozing of blood and enough mechanical separation of the cavity walls occurs to allow the movement of the endoscope. Similarly, the cavity flow rate should be adequate enough to constantly wash away blood and tissue debris in order to allow clear vision. Many prior systems utilize a peristaltic pump over the inflow and or the outflow side and these peristaltic pumps create pressure pulsations which are then transmitted to the tissue cavity. Such pressure pulsations are undesirable and the main aim of the present invention is to dampen such pressure pulsations.

A Safe Distending System

An efficient distending system as explained in the previous paragraph need not also be a safe distending system. In this regard, the Inventors would like to highlight that if the cavity pressure rises above the prescribed safe limits excessive fluid intravasation may occur or the cavity may even burst. Fluid intravasation is a process by which the irrigation fluid enters into the patient's body system through the cavity walls and may cause significant danger to the patient's life including death. Thus a safe distending system is one which prevents or minimizes fluid intravasation and allows the surgeon to accurately know the instantaneous real time rate of fluid intravasation into the patient's body system.

No Prior Art is Absolutely Safe

Many different types of uterine distending systems are known and are being commercially marketed by many different companies but none of these systems can be considered to be absolutely safe for the patient. This fact has been clearly stated in the 'Hysteroscopic Fluid Monitoring Guidelines proposed by the Ad Hoc Committee on Hysteroscopic Fluid Guidelines of the American Association of Gynecologic Laproscopists February 2000 (Loffler F D, Bradley L D, Brill A I et al: Hysteroscopic fluid monitoring guidelines. The journal of the Americal Association of Gynecologic Laproscopists 7(1): 167-168, 1994) where the authors clearly and explicitly state "fluid pumps for low-viscosity media are a convenience and do not guarantee safety". The present invention aims at providing a distending system which is both safer and more efficient in comparison to all the prior art systems.

Basic Physics of Cavity Distension

Although, a person skilled in the art may know it, the Inventors would like to provide a brief description of the basic physics of cavity distension. Filling the tissue cavity with fluid enables distension of the same. Initially more fluid is pumped in than the amount which is extracted from the cavity and ultimately the inflow rate is fixed at a level where a somewhat desired cavity pressure and distension is achieved. It may be possible to accurately maintain the desired pressure and distension in the case of a rigid cavity, for example a cavity made of steel.

However, the body tissue cavities are not rigid because they are distensible and also have some element of elasticity. Thus a distended tissue cavity in its attempt to constantly revert back to its natural collapsed state reacts by exhibiting physiological contractions of the cavity wall which generally leads to variations in the cavity pressure which ultimately culminates in irregular movement excursions of the cavity walls. In a static system the said movement excursions may be so minute that they may even go unnoticed. However in a dynamic system such that being created during an endoscopic procedure, the said physiological cavity wall contractions may cause the cavity to expel out its entire fluid content thus leading to a surgically dangerous large magnitude movement excursion of the cavity wall. Because of these reasons it is extremely difficult to maintain the cavity pressure and cavity distension in a predictably stable fashion.

Further, the inflow tube, the out flow tube and the endoscope also invariably move and shake during surgery which leads to variations in fluid flow resistance which is also manifested in the form of variations in the cavity pressure. The cavity pressure variations occurring as a result of cavity wall contractions and the mechanical movement of the tubes and the endoscope tend to occur again even if they are corrected once because it is impossible to prevent the physiological cavity wall contractions and the mechanical movements of the irrigation circuit. Thus, the said cavity pressure variations shall continue to occur even after multiple repeated corrections.

Thus, till date the surgeon was only left with two options, either to ignore the said cavity pressure variations by not correcting them, or to externally and actively correct such pressure variations. The Inventors have noticed that any attempt to externally and actively correct the said cavity pressure variations leads to an undesirable turbulence inside the cavity and also tends to amplify the resultant movement excursions of the cavity walls. Thus there is a grave need to provide a system which can maintain an almost constant and stable cavity pressure even in the presence of the said physiological cavity contractions and the mechanical movements in the irrigation circuit.

Brief Description of an Endoscope

Prior to describing the basic layout of a continuous flow irrigation system the basic structure of an 'endoscope' needs to be described. Endoscope is a cylindrical tube having an outer diameter ranging between 3 to 9 mm approximately. A typical endoscope has four channels. One channel is meant to pass a fibereoptic telescope while endoscopic instruments are negotiated through a second instrument channel. A third channel also known as the inflow channel is used for pushing irrigation fluid into a tissue cavity, the proximal end of this channel ending in a metal adaptor known as the inflow port while the distal end of this inflow channel opens near the tip of the endoscope. The inflow port is connectable to an inflow tube which carries sterile irrigation fluid from a fluid source reservoir. A fourth channel also known as the out flow channel is meant for extracting waste fluid out of the cavity, the proximal end of this channel ending in a metal adaptor known as the outflow port while the distal end of this outflow channel opens near the tip of the endoscope. The outflow port is connectable with an outflow tube which transports the waste fluid from the cavity to a suitable waste fluid collecting reservoir. A set of fiber optic bundles contained inside the telescope transmit light energy produced by an external light source. This light energy illuminates the walls of the tissue cavity. The image thus formed is carried via a separate set of optical pathways again situated inside the telescope. A video camera attached to the eye piece of the telescope forms a clear endoscopic image of the cavity on a TV monitor. The endoscopic surgeon has to continuously look at the TV monitor all through the endoscopic procedure.

Basic Layout of a 'Continuous Flow Irrigation System

Henceforth in this manuscript unless otherwise specified the term 'distension' shall be deemed to imply tissue cavity distension by 'continuous flow irrigation' only and the term 'cavity' unless specifically stated shall be deemed to refer to a 'body tissue cavity'. In a typical distension system a physiological non viscous liquid like 0.9% normal saline, 1.5% glycine, mannitol, ringer's lactate and 5% dextrose is stored in a sterile fluid source reservoir. A fluid supply tube connects the said fluid reservoir with the inlet end of a pump. The outlet end of the inflow pump is connected to the inflow port of an endoscope. When the inflow pump operates the fluid from the fluid source reservoir is sucked via the fluid supply tube and the inflow pump pushes this fluid into the tissue cavity via the said inflow tube. The pump operates by consuming certain amount of energy and as a result of this a positive fluid pressure is created inside the tissue cavity. An outflow tube extends between the outflow port and the inlet end of an outflow pump. When the outflow pump operates it actively extracts waste fluid from the cavity again at the expense of energy and this waste fluid is ultimately sent to a waste fluid reservoir via a tube which connects the outlet end of the outflow pump with the waste fluid reservoir. Alternatively the outflow pump may be missing and in such case the outflow tube directly carries the waste fluid from the cavity to the waste fluid reservoir and the energy for such act is supplied by gravity instead of the outflow pump. Also, the inflow pump may be missing and in such case the inflow tube directly supplies the irrigation fluid from a fluid source reservoir to the cavity. In such case the fluid source reservoir is hung at a suitable height above the patient and the said energy for cavity distension is derived from gravity instead of the inflow pump. A suitable pressure transducer is attached to the inflow tube, the outflow tube or directly to the cavity to measure the fluid pressure. A controller may be incorporated to regulate the system.

The Simplest Continuous Flow Irrigation System

In its simplest form, a continuous flow irrigation system comprises a fluid reservoir bottle hung at a suitable height above the patient and an inflow tube connecting this fluid reservoir to a tissue cavity. An out flow tube is incorporated to remove fluid from the tissue cavity. In this system there is no pump and no transducer. In such a system fluid flows from the fluid source reservoir into the cavity and the required energy is supplied by gravity. The pressure developed inside the cavity can be increased or decreased by elevating or lowering the height of the fluid source reservoir. In such system the main limiting factor is the height of the room ceiling beyond which the fluid reservoir cannot be raised. This is a crude system having negligible practical importance and has been included only from the academic point of view. Also in such a system unlimited volume of irrigation fluid may enter into the patient's blood circulation. Thus such system is not suitable even from the patient safety point of view.

Basic Components of a Continuous Flow Irrigation System

Like a motor car is made up of certain obvious components like engine, tyres and a steering wheel, a continuous flow distending system is made of components like pump, pressure transducer, flow regulating valve, rubber tubes and a controller. The pump may be a positive displacement pump like a peristaltic pump, piston pump or a gear pump or alternatively it may be a dynamic pump like a centrifugal pump. Further the said pump may be of a fixed RPM type which runs at fixed RPM all through the endoscopic procedure or the pump may be of a variable RPM type which operates at variable RPM during the endoscopic procedure. It is extremely important to note that fixed RPM pumps and variable RPM pumps are two separate mechanical entities in context with a cavity distending system because the fixed and variable RPM pumps impart different surgical efficiency and patient safety criteria to the distending system. The said pump may be attached on the inflow side only, on the outflow side only or both on the inflow and outflow side. Further if a pump is attached only on the inflow side the outflow tube may directly empty in a waste fluid reservoir at atmospheric pressure or a vacuum source may also be additionally attached. In some distending systems a flow controlling valve is attached on the outflow tube in order to regulate the cavity pressure. There may be a single pressure transducer attached to the inflow tube, the outflow tube or directly to the cavity. In some systems instead of one pressure transducer two pressure transducers may be used, one on the inflow tube and the other on the outflow tube.

Relvant references have been included in a PCT application filed by us in the past however three additional references are now being included. These references are U.S. Pat. No. 5,520,638, U.S. Pat. No. 4,902,277 and U.S. Pat. No. 5,578,012.

In the U.S. Pat. No. 5,520,638 a variable speed peristaltic pump is used to push irrigation fluid into a tissue cavity. This patent is related to the 'Continuous Wave II Arthroscopy Pump' marketed by Arthrex. A chamber with volume is connected to the inflow tube and a collapsible bladder is contained within the bladder. The collapsible bladder has an open end connected with tubing to a pressure transducer. Once activated the pump begins to introduce fluid into the tissue cavity via the inflow tube and as pressure builds within the tissue cavity, fluid enters the chamber, and air in the chamber is compressed. The compressed air in the chamber compresses the bladder. Air pressure in the bladder is experienced by the pressure transducer. The pressure transducer feeds pressure information to a controller which regulates the RPM of the pump on the basis of a pressure feedback mechanism. Thus by the help of a pressure feedback mechanism the pressure inside a tissue cavity is maintained by fluctuating around a desired value. In this invention an important purpose of the said chamber is to dampen the pressure pulsations created by the peristaltic pump. Such pressure pulsations create turbulence inside the tissues cavity and are hence undesirable. The method of dampening the pressure pulsations as described in this U.S. Pat. No. 5,520,638 is not adequately efficient, especially at high pump RPM's. In the present invention a method shall be described by which the amplitude of the said pressure pulsations would be reduced to negligible magnitude even at a high pump RPM.

In U.S. Pat. No. 4,902,277 a pump is provided on the inflow side which pushes fluid into a tissue cavity while a positive displacement pump removes fluid from the cavity. This patent is related to 'FMS duo Fluid Management System' marketed by FMS Group. By the help of a pressure feedback mechanism the inflow pump is constantly increased or decreased thereby maintaining the cavity around a desired value. Thus by the help of a pressure feedback mechanism the pressure inside a tissue cavity is maintained by fluctuating around a desired value.

In U.S. Pat. No. 5,578,012 a centrifugal pump is deployed on the inflow side while no pump is deployed over the outflow side. This patent is related to the 'HydroFlex HD' pump marketed by DAVOL company. By the help of a pressure feedback mechanism the inflow pump is constantly increased or decreased thereby maintaining the cavity around a desired value. Thus by the help of a pressure feedback mechanism the pressure inside a tissue cavity is maintained by fluctuating around a desired value.

OBJECTS OF THE INVENTION

The overall objective of the invention is to provide a safe, efficient and turbulence free system for distending body tissue cavities for those endoscopic procedures which utilize continuous flow irrigation.

The main object of the invention is to minimize the amplitude of pressure pulsations, inside the tissue cavity, created by an outflow positive displacement pump to almost negligible levels, irrespective of the outflow pump RPM.

Another object of the invention is to minimize the frequency of pressure pulsations, inside the tissue cavity, created by an outflow positive displacement pump, without reducing the outflow pump RPM.

Another object of the present invention is to provide a system for distending tissue cavities using which it being possible to create and maintain a desired precise cavity pressure for a desired precise rate at which fluid may be allowed to flow through the cavity, for any length of time.

Still another object of the present invention is to provide a system for distending tissue cavities using which it being possible to achieve a predictably constant clear endoscopic vision throughout the endoscopic procedure.

Yet another object of the present invention is to provide a system for distending tissue cavities using which it being possible to achieve a predictably stable mechanical cavity distension throughout the endoscopic procedure.

One more object of the present invention is to provide a system for distending tissue cavities using which it being possible to predictably maintain the cavity pressure at any desired precise value despite physiological contractions of the cavity wall.

One another object of the present invention is to provide a system for distending tissue cavities using which it being possible to constantly, accurately and reliably determine the instantaneous real time rate of fluid intravasation into the patient's body by using hot wire anemometer type of fluid rate sensors.

A further more object of the present invention is to provide a system for distending tissue cavities using which it being possible to maintain any desired precise and high cavity pressure without increasing the 'maximum possible fluid intravasation rate'.

Another object of the present invention is to provide a system for distending tissue cavities using which it being possible to measure the actual cavity pressure, in an accurate, reliable and simple manner, by using a pressure transducer located far away from the cavity in the up stream portion of the inflow tube.

Yet another object of the present invention is to provide a system for distending tissue cavities using which it being possible to make the pressure inside the body cavity and the flow rate of the fluid passing through the body cavity absolutely independent of each other such that the value of any may be altered without affecting the value of the other.

One more object of the present invention is to provide a system for distending tissue cavities using which it being possible for the surgeon to have a fairly accurate assessment of the total volume of the irrigation fluid which would be required to complete the entire endoscopic procedure.

SUMMARY OF THE INVENTION

The main aim of the present invention is to minimize fluid turbulence inside a tissue cavity during endoscopic procedures. The present invention is a safe and an efficient system for distending body tissue cavities for those endoscopic procedures which utilize continuous flow irrigation. In the present invention an inflow pump driven by a solenoid devise is used to instill fluid into a tissue cavity while a positive displacement pump, like a peristaltic pump, is used for simultaneously extracting waste fluid out of the tissue cavity. In the present invention the amplitude of tissue cavity pressure fluctuations caused by the positive displacement outflow pump can be minimized to almost negligible levels. The pressure frequency of the said pressure pulsations can also be reduced. The present invention is a system of creating and maintaining a desired positive pressure inside a body tissue cavity through which fluid can be made to flow at a desired fixed flow rate. Alternatively the present invention may be considered as a system of creating cavity fluid pressure which is absolutely independent of the cavity outflow rate. Also in the proposed invention the changes in the tissue cavity pressure are not actively corrected as is done in many prior art systems. Also the same system can be used for multiple endoscopic procedures which utilize continuous flow irrigation.

DETAILED DESCRIPTION OF INVENTION

Figure 1:
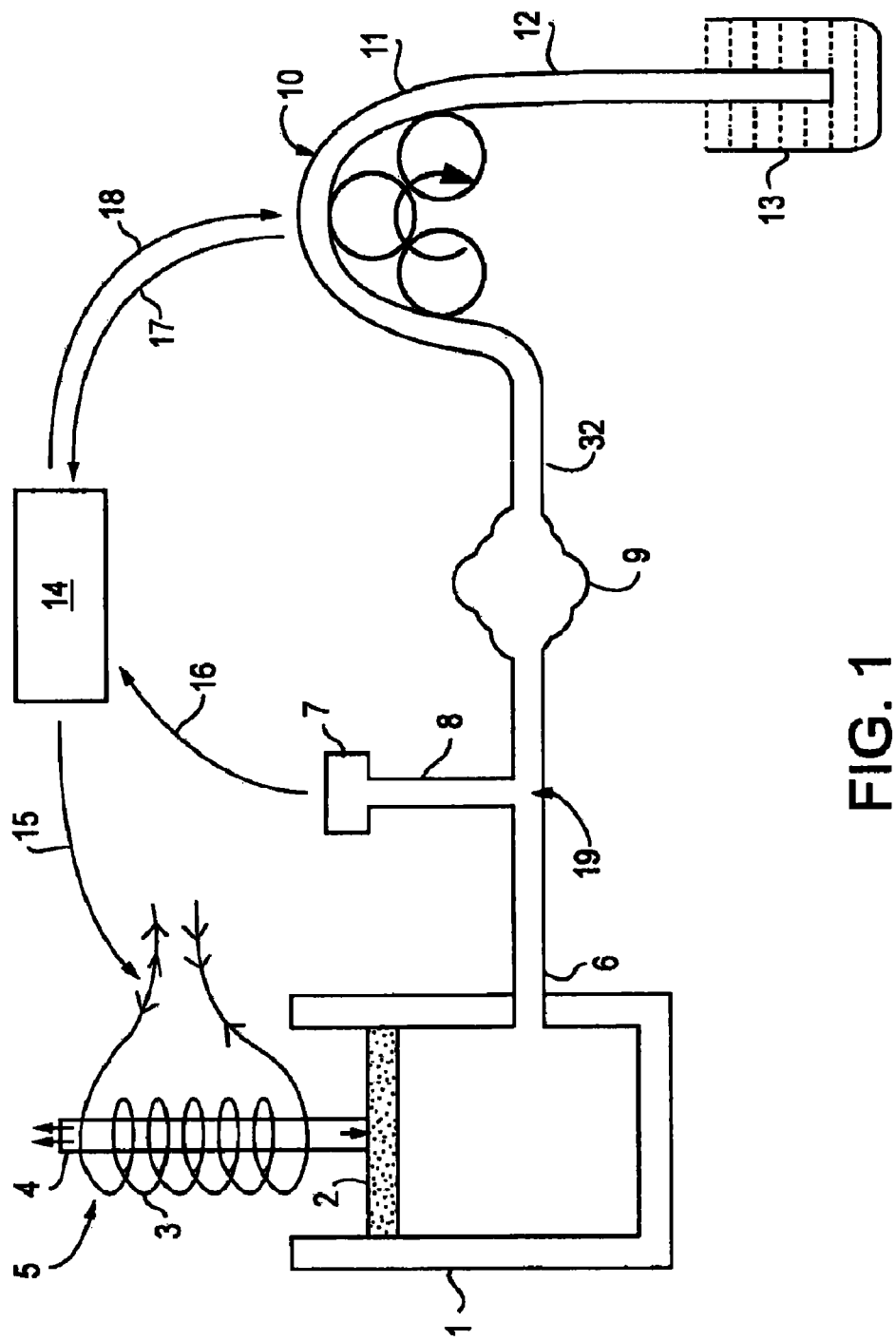
FIG. 1 shows the basic layout of the invention of the invention without the 'pressure pulse dampening system'.

Accordingly, the present invention provides a system for distending body tissue cavities of subjects by continuous flow irrigation during endoscopic procedures the said system comprising: a syringe shaped fluid source reservoir containing a non viscous physiologic fluid meant for cavity distension; an outlet port of the syringe shaped fluid source reservoir being connectable to an inflow port of an endoscope instrument via an inflow tube for dispensing the fluid at a controlled flow rate into the cavity, the flow rate at which the fluid enters into the cavity being termed as the cavity inflow rate; an inflow pressure transducer being located anywhere in the inflow tube for measuring the fluid pressure inside the cavity, an outflow port of the endoscope being connectable to an inlet end of a variable speed positive displacement outflow pump through an outflow tube for removing the fluid from the cavity at a controlled flow rate, the flow rate of the said outflow pump being termed as the cavity outflow rate, and an outlet end of the outflow pump being connected to a waste fluid collecting container through a waste fluid carrying tube, characterized in that the syringe shaped fluid source reservoir comprises of a hollow barrel for holding the fluid, a plunger mechanism mounted slidably inside the barrel for dispensing the fluid and the plunger being provided with an electromagnetic means for slidably moving the plunger mechanism in a to and fro direction inside the barrel.

In an embodiment of the present invention, a proximal end of the inflow tube is connected to the outlet port of the syringe shaped fluid source reservoir and a distal end of the inflow tube being connectable to the inflow port of the endoscope instrument.

In another embodiment of the present invention, the inflow pressure transducer is located sufficiently away from the cavity site, preferably near the outlet port of the syringe shaped fluid source reservoir from the practical point of view, such that the actual pressure inside the cavity is measured.

In yet another embodiment of the present invention, a proximal end of the outflow tube being connectable to the outlet port of the endoscope instrument and a distal end of the outflow tube is connected to an inlet end of the variable speed positive displacement outflow pump.

In still another embodiment of the present invention, the variable speed positive displacement outflow pump is selected from the group comprising peristaltic pump, piston pump, gear pump and diaphragm pump.

In one more embodiment of the present invention, the variable speed positive displacement outflow pump is a peristaltic pump.

In one another embodiment of the present invention, the syringe shaped fluid source reservoir comprises a hollow barrel with a proximal open end and a partially closed distal end forming an outlet port; a plunger mechanism comprising a piston and a magnetic rod being slidably provided inside the barrel and the electro magnetic means comprising a coil made of insulated conducting wire being loosely wound around the magnetic rod.

In a further embodiment of the present invention, the coil is connected to a DC current supplying means.

In a further more embodiment, the system of the present invention further comprises a microcontroller electrically coupled to the inflow pressure transducer, the outflow positive displacement pump and the electro magnetic means for controlling the cavity inflow and cavity outflow rates.

In another embodiment, the system of the present invention further comprises an inflow housing tube having a controllable constriction site, a distal end of the same being connected to the inflow tube to provide an exit route for any excess fluid present inside the tissue cavity or being dispensed by the syringe shaped fluid source reservoir, thereby minimizing turbulence inside the body tissue cavity and maintaining the body tissue cavity pressure at a stable value despite physiological contractions of the body tissue cavity wall.

In yet another embodiment of the present invention, the inflow housing tube is releasably connected on the inflow tube to enable replacement of the housing tube with yet another housing tube having a different diameter at the constriction site to suit the operational need of the endoscopic procedure.

In still another embodiment of the present invention, a distal end of the inflow housing tube is connected to the inflow tube near its proximal end close to the outlet port of the syringe shaped fluid source reservoir.

In one more embodiment of the present invention, a proximal end of the inflow housing tube empties directly into a excess fluid collecting container and is constantly and completely immersed in the said container.

In one another embodiment of the present invention, the inflow housing tube is provided with a clamping means at the constriction site to enable the user to vary the diameter of the housing tube at the constriction site to suit the operational needs of endoscopic procedures.

In a further embodiment of the present invention, the inflow housing tube is provided with an electromechanical device, a solenoid, to enable the micro-controller to vary the diameter of the constriction site.

In a further more embodiment of the present invention, the diameter of the inflow housing tube at the constriction site is in the range of 0.001 mm to a maximum value which is less than the overall diameter of the rest of the housing tube In one further embodiment of the present invention, the diameter of the inflow housing tube at the constriction site is in the range of 0.01 to 2.5 mm.

In an embodiment, the system of the present invention further comprises a fluid replenishing container connected to the syringe shaped fluid source reservoir for refilling the fluid source reservoir.

In another embodiment of the present invention, the excess fluid collecting container is optionally connected to the syringe shaped fluid reservoir for reusing the fluid collected in the excess fluid collecting container.

In yet another embodiment of the present invention, the fluid replenishing container or the excess fluid collecting container is connected to the syringe shaped fluid reservoir by a fluid supply tube.

In still another embodiment of the present invention, the fluid replenishing container or the excess fluid collecting container is connected to the syringe shaped fluid reservoir via a replenishment pump and a fluid supply control valve.

In a further embodiment of the present invention, an inflow fluid controlling valve is provided on the inflow tube for preventing the fluid from entering into the tissue cavity during fluid replenishment phase.

In a further more embodiment of the present invention, the replenishment pump, the fluid supply control valve and the inflow fluid controlling valve are optionally coupled to the microcontroller.

In another embodiment, the system of the present invention, further comprises an outflow pressure transducer connected between a proximal end of the outflow tube and the inlet end of the variable speed positive displacement outflow pump for measuring the pressure in the outflow tube.

In yet another embodiment of the present invention, the outflow pressure transducer is optionally electrically coupled to the microcontroller.

In still another embodiment, the system of the present invention further comprises an outflow housing tube having a variable size constriction site being provided between the outflow tube and the waste fluid reservoir.

In one more embodiment of the present invention, a proximal end of the outflow housing tube is connected to the outflow tube near the inlet of the outflow pump.

In one another embodiment of the present invention, a distal end of the outflow housing tube is connected to the waste fluid carrying tube or to the waste fluid collecting reservoir.

In still another embodiment of the present invention, the outflow peristaltic pump is provided with 1 to 5 peristaltic pump tubes connected in parallel between the inflow and the outflow ends of the peristaltic pump for reducing the frequency of pressure pulsation, the said tubes being connected to each other at the inflow and the outflow ends of the peristaltic pump and the said peristaltic pump tubes being the ones which come in contact with the rollers of the peristaltic pump.

In yet another embodiment, the system of the present invention further comprises an outflow pressure pulsation dampening means connected to the outflow tube for dampening the pressure pulsations inside the body tissue cavity caused by the outflow peristaltic pump.

In a further embodiment of the present invention, the outflow pressure variation dampening means comprises a single outlet syringe mechanism, the piston of the same being coupled synchronously to the positive displacement outflow pump through a coupling means and the single outlet end of the said syringe mechanism being connected to the outflow tube.

In one more embodiment, the system of the present invention further comprises a fluid inflow rate sensor connected to the inflow tube.

In one further embodiment of the present invention, the fluid inflow rate sensor is located in the lumen or wall of the inflow tube for measuring the cavity inflow rate.

In another embodiment, the system of the present invention further comprises a fluid outflow rate sensor connected to the outflow tube.

In yet another embodiment of the present invention, the fluid outflow rate sensor is connected between the proximal end of the outflow tube and the inlet end of the variable speed positive displacement outflow pump for measuring the cavity outflow rate.

In still another embodiment of the present invention, the fluid outflow rate sensor is located in the lumen or wall of the outflow tube for measuring the cavity outflow rate.

In a further embodiment of the present invention, the fluid inflow and the outflow rate sensors consist of a heating coil in physical contact with a metal plate for heating the same and a temperature sensor placed in contact with the metal plate for measuring the temperature of the said metal plate, the temperature of the metal plate being a function of the fluid flow rate.

In a further more embodiment of the present invention, the fluid rate flow sensor is a hot wire anemometer.

In one further embodiment of the present invention, instantaneous real time rate of fluid intravasation is determined by electrically connecting the inflow and outflow fluid flow rate sensors to a micro-controller.

In an embodiment of the present invention, the fluid supply tube, the inflow tube, the outflow tube and the waste fluid carrying tube are flexible, disposable and are made of polymeric material.

The proposed invention is described hereafter with reference to the accompanying drawings in order to clearly explain and illustrate the system and the working of the system. It is respectfully submitted the scope of the invention should not be limited by the description being provided hereafter.

The system of the present invention is a unique system for distending body tissue cavities in endoscopic procedures. In the proposed invention a pump operated by solenoid type of electromechanical means is used on the inflow side while a positive displacement pump like a peristaltic pump is used on the outflow side. In the proposed invention a body tissue cavity is distended by continuous flow irrigation in such a manner that the amplitude as well as the frequency of the said pressure pulsations created by the positive displacement outflow pump can be minimized. Also the cavity pressure is absolutely independent of the cavity outflow rate, such the both, the cavity pressure and the outflow rate, may be independently altered without varying the value of the other parameter.

In FIG. 1 a cylindrical fluid source reservoir 1 represented by thick shaded walls contains a non viscous sterile physiological fluid like 0.9% normal saline, 1.5% glycine, ringer lactate or 5% dextrose fluid. A piston 2 is represented by a dotted area. This piston is attached to a cylindrical magnetic rod 4. The magnetic rod 4 may be a permanent magnet and besides being circular it may also be a square or quadrilateral in its cross section. The magnetic rod 4 is freely placed inside the lumen of coil 3. The coil 3 is made up of suitable number of turns of an insulated wire, such as copper wire. The magnetic rod 4 is so placed inside the coil 3 that it can move freely inside the coil, that is in or out of the coil. Like any other permanent magnet, the permanent magnet 4 also has a magnetic polarity, that is a north pole and a south pole. When DC current passes through the coil, the coil also develops a magnetic polarity as a result of which the magnetic rod 4 is linearly displaced in one of the two possible directions, that is in a direction towards the piston represented by a single arrow or in a direction away from the piston represented by double arrows. The direction of linear excursion of the magnetic rod 4 shall depend upon the relative magnetic polarities of the magnet 4 and the coil 3. As the magnetic polarity of coil 3 depends upon the direction of current which passes through the coil thus in accordance to the laws of physics it can be inferred that the direction of movement of the magnetic rod 4 also depends upon the direction of current flow through the coil. The directions of the current flow through the coil is denoted by arrows situated on the two ends of the wire which forms the coil. Obviously current can flow only in two directions, one direction being denoted by a pair of single arrows and an opposite direction being denoted by a pair of double arrows. In the rest of the manuscript it shall be assumed that if the current flows in the direction of single arrows then the magnetic rod 4 moves in the direction of the single arrow that is towards the piston as a result of which the piston presses over the irrigation fluid contained inside the container 1 which compresses the fluid as result of which a positive pressure is created in the fluid inside the container 1. Let it be assumed that the piston 2 makes a fluid tight contact with the walls of the container 1 such that no fluid escapes through the potential space between the piston and the walls of container 1. Let it also be assumed that the piston can freely move inside the cylindrical container 1 without friction. Let the magnitude of current passing through the coil be denoted by C and the resultant force which the magnetic rod 4 applies to the piston 2 be termed as F. As just discussed, a current flowing in the direction of the single arrows tends to move the magnetic rod in the direction of a single arrow situated at the lower end of the magnetic rod and in this manner the magnetic rod 4 exerts a force F on the piston 2. If the total surface area of the piston is A then the pressure P exerted by the piston on the irrigation fluid inside container 1 shall be F divided by A. Again referring to FIG. 1, the pressurized irrigation fluid escapes via an inflow tube 6 and enters into the tissue cavity 9. A pressure transducer 7 is attached at one of a tube 8 while the other end of tube 8 is connected anywhere on inflow tube 6. For practical convenience it is desirable that the said other end of tube 8 be connected in the up stream part of the inflow tube 6 such as at point 19. For practical convenience the point 19 may be located in the pump housing itself. The pressure transducer 7 measures the fluid pressure via a column of liquid or air present in the lumen of tube 8 and is considered to be the same as the fluid pressure inside the container 1 and the fluid pressure inside the tissue cavity 9. The fluid pressure as measured by the pressure transducer 7 shall be referred to as P. In this manuscript the term 'P' shall frequently be used to refer to the actual pressure inside the tissue cavity but in physical terms P is the pressure sensed by the transducer 7 at point 19. The pressure transducer 7 may also be in the form of a membrane diaphragm incorporated in the wall of the inflow tube 6 such that this membrane diaphragm is in direct contact with the fluid contained in the inflow tube 6, such that the linear movement excursions of the said membrane are interpreted as pressure of the fluid inside the inflow tube 6 by a suitable pressure transducer. Such type of pressure sensor being directly incorporated in the wall of the inflow tube 6 senses the fluid pressure without the intervention of tube 8. The basic purpose of the transducer 7 is to measure the fluid pressure inside the inflow tube 6, such as at point 19, thus the mechanical construction of the transducer is not important as long as it measures the fluid pressure. For the sake of simplicity the existence of tube 8 shall be continued to be considered in the rest of the manuscript.

An outflow tube 32 actively extracts waste fluid out of the cavity 9. One end of the outflow tube is connected to the tissue cavity 9, usually via an outflow port of an endoscope, the other end of the said outflow tube is connected to the inlet end of a positive displacement pump, preferably a peristaltic pump 10 as shown in FIG. 1. The tube over which the rollers of the peristaltic pump 10 move is labeled as 11 and this tube can be made of any suitable resilient plastic material. Thus the outflow tube 32 extends between the outlet end of the cavity 9 and the inlet end of peristaltic pump tube 11. The outlet end of the peristaltic pump tube 11 is connected to a waste fluid drainage tube 12. The distal open end of the waste fluid drainage tube 12 opens into a waste fluid collecting container 13 at atmospheric pressure. The direction of rotation of the pump 10 is denoted by a curved arrow. Hence forth in this manuscript the flow rate of the outflow pump 10 shall be termed as R2 while the rate at which the pressurized fluid enters from the container 1 into the inflow tube 6 shall be termed as R1.

Again in reference with FIG. 1 the system comprising of the magnetic rod 4 and coil 3 shall be termed as 'electro magnetic devise' which has been labeled as 5. A controller 14 receives pressure related information via wires 16. A rotation counting devise such as a suitable tachometer, not shown in the diagrams, is coupled to the out flow pump 10 and pump rotation related information is sent to the controller 14 via wires 17. The controller regulates the RPM of pump 10 via wires 18. The flow rate of the outflow pump 10 is directly proportional to the pump RPM thus the RPM related information as received from the said tachometer actually sends flow rate related information to the controller 14. The controller regulates the force F exerted by the 'electromagnetic devise' 5 via wires 15 and such is accomplished by varying the magnitude or direction or both of the current passing through the coil 3 or by varying the voltage applied across the two ends of the coil 3.

In order to understand the invention in a simpler manner it is assumed that all tubes, containers and components shown in FIGS. 1 to 6 are placed at the same horizontal height with respect to the ground.

Again referring to FIG. 1, at the start of the endoscopic procedure the outflow pump is set to work at a desired flow rate R2 by feeding in the value of the said desired outflow rate into the controller 14 via suitable input means. A desired pressure value P is also similarly fed into the controller 14 via suitable display means. On the basis of a pressure feedback mechanism the controller 14 causes the 'electromagnetic devise' 5 to push the piston 2 in a downward direction such that a positive pressure is created and is maintained throughout the endoscopic procedure. If the controller senses a fall in the cavity pressure then a suitable signal is sent via wires 15 to increase the force F being applied by the electromagnetic devise over the piston 2 so that the cavity pressure increases to the initially desired value P. Similarly if the controller senses a rise in the cavity pressure then a suitable signal is sent via wires 15 to decrease the force F being applied by the electromagnetic devise over the piston 2 so that the cavity pressure decreases to the initially desired value P. In this manner the cavity pressure is maintained by fluctuating around a desired value P.

Figure 2:
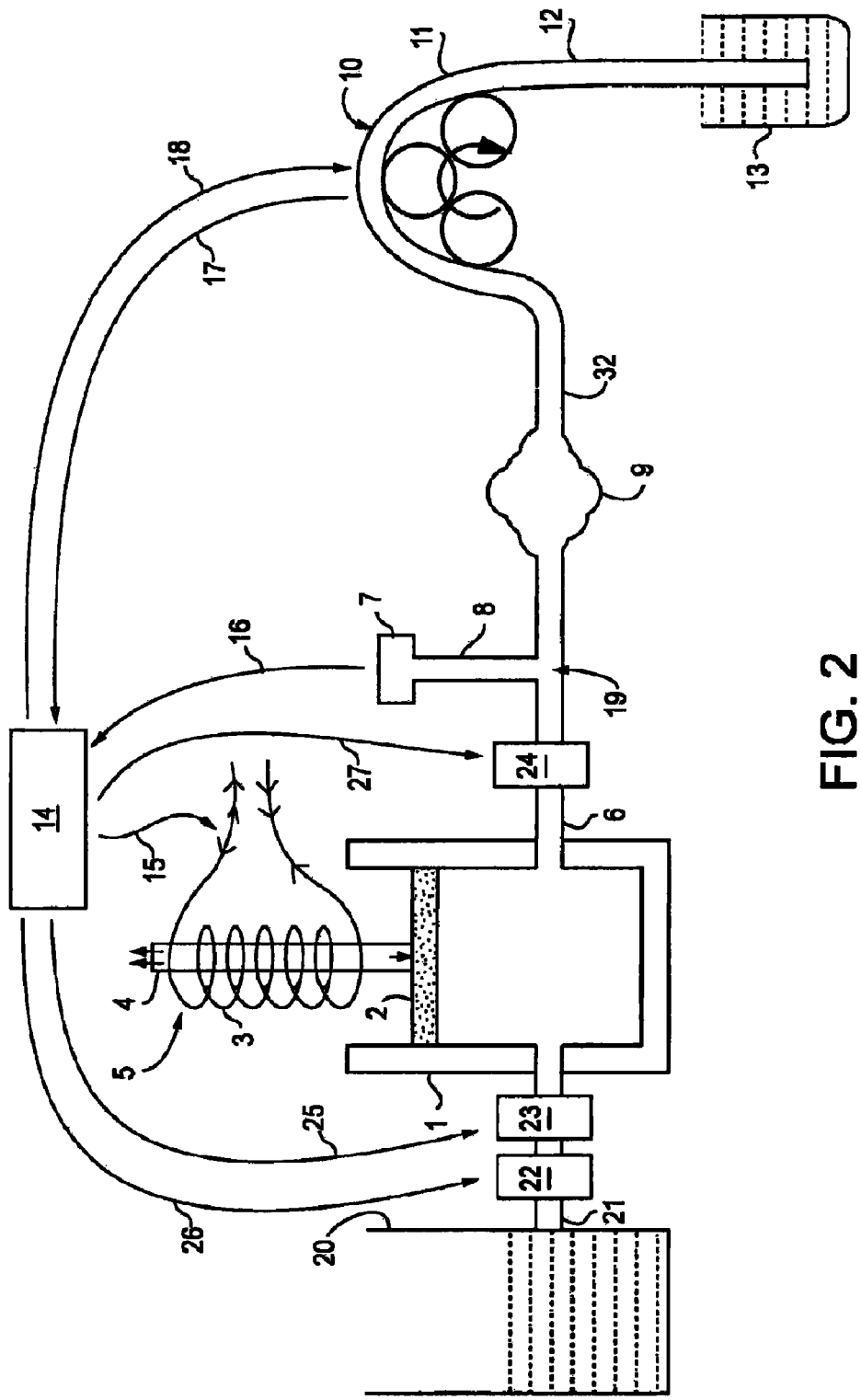
FIG. 2 is similar to FIG. 1 except that a fluid source reservoir 20 and fluid controlling valves 23, 24 and a fluid replenishing pump 22 have been included.

Referring to FIG. 2, this figure is the same as FIG. 1 except that a fluid source reservoir 20, a fluid supply tube 21, a pump 22 and two fluid controlling valves 23 and 24 have also been incorporated. The fluid supply tube 21 extends between the fluid source reservoir 20 and the container 1. Sterile irrigation fluid can be added into the container 20 as and when required during an endoscopic procedure and this fluid can be used for replenishing the fluid inside the container 1 by the help of pump 22. A pump 22 and a flow controlling valve 23 have been incorporated over the fluid supply tube 21. Similarly a flow controlling valve 24 has been incorporated over the inflow tube 6. The pump 22 can be any suitable pump which can pull fluid from the fluid source reservoir 20 at atmospheric pressure and push it into the container 1. The pump 22 can be a dynamic pump like a centrifugal pump or it can be a positive displacement pump like a peristaltic pump or a piston pump. The switching on or off and the RPM of the pump 22 can be regulated by the controller 14 via wires 26 while the opening or closing of valves 23 and 24 is regulated by the controller via wires 25 and 27 respectively. The valves 23 and 24 function to either completely occlude or to completely open the lumen of the respective tubes 21 and 6. The opening or closing functions of valves 23 and 24 can be carried out by a suitable devise such as a solenoid operated devise installed over the respective tubes and such solenoid operated devise can be operated under the influence of the controller. The container 1 as shown in FIG. 1 has a limited volume capacity and the total fluid contained in it may be consumed quickly during a surgical procedure and in order to solve this problem the system as shown in FIG. 2 has been proposed. Again in context with FIG. 2 the controller may be so programmed that on the basis of a single command three actions would occur simultaneously and these three actions are as follows:

1. The valve 24 completely occludes the lumen of the inflow tube 6.
2. The valve 23 completely opens the lumen of tube 21.
3. The pump 22 immediately starts operating at a desired RPM in order to push fluid into the container 1.

As a result of the above three actions the container 1 can be replenished intraoperatively in any desired short time interval. It is also possible to programme the controller in a manner that a single common signal for all the above three functions could be automatically generated on the basis of a feedback such as optical or electrical means, which would sense the level of the residual fluid in container 1, so that a signal is triggered the moment the level of fluid in container 1 falls below a predetermined critical low level.

Figure 3:
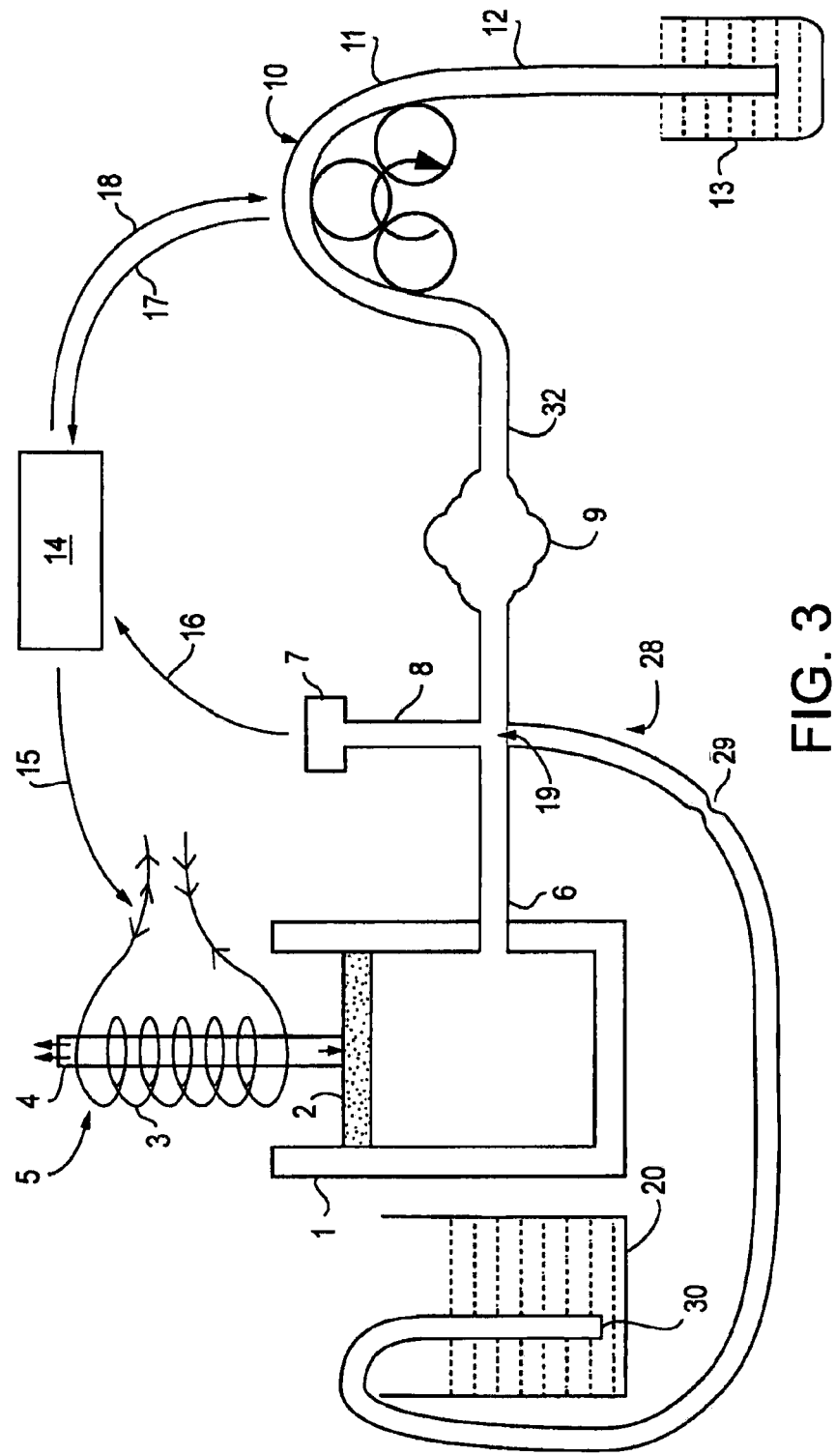
FIG. 3 is similar to FIG. 1 except that a constriction site housing tube 28 has been included.

In context with the systems shown in FIGS. 1 and 2 the cavity pressure is maintained by irregularly fluctuating around a desired preset pressure value because the controller constantly attempts to correct even minor variations in the cavity pressure, which ultimately leads to undesirable turbulence inside the cavity. In order to avoid the said turbulence a system shown in FIG. 3 is being suggested. The system shown in FIG. 3 is basically the same as the system shown in FIGS. 1 and 2 except for the fact that in FIG. 3 a constriction site housing tube 28 had been also been included. One end, that is the distal end, of this tube 28 is connected anywhere along the inflow tube 6 such as at a point 19 while the proximal free end of this tube labeled as 30 drains into a fluid source reservoir such that point 30 lies at the most dependent part of the container 20. The said constriction site housing tube 29 has a constriction point 29 which can be located anywhere along its length. Such constriction point refers to a point at which the inner diameter of the lumen of tube 28 is reduced in comparison to the lumen of the rest of the tube 28. Such constriction may be a permanent constriction in the lumen of tube 28 or it may be a variable constriction whose diameter may be increased or decreased as desired.

Again referring back to FIG. 3 when the 'electro magnetic devise' 5 is activated the piston is pushed down and fluid starts entering into tubes 6, 8, 28 and into the cavity 9. If the distal end of the inflow tube is occluded by closing the inflow port of the endoscope and the constriction site 29 is also fully occluded, fluid starts accumulating inside tubes 6, 8, and inside a part of tube 28 between point 19 and the constriction site 29. If tube 28 continues to remain fully occluded at the constriction site 29, the fluid continues to accumulate inside tubes 6, 8, and inside a part of tube 28 between point 19 and the constriction site 29, as result of which the pressure transducer 7 reads a steeply increasing fluid pressure. The moment the block at the constriction site 29 is partially released fluid escapes in the form of a jet through the partially open constriction opening 29 in the direction of point 30. With the constriction opening 29 being only partially blocked and with the 'electro magnetic devise' continuously exerting a constant force on the piston 2 the pressure P as sensed by the transducer 7 ultimately gets stabilized at a fixed value provided the internal diameter of the constriction site 29 is not further varied. The diameter D of the constriction site 29 ranges from a minimum non-zero value to a maximum value which is less than the overall diameter of the rest of the housing tube 28. Henceforth in this manuscript the inner diameter of the constriction site 29 shall be deemed to be fixed at some predetermined value D, unless otherwise stated.

Again referring back to FIG. 3, the surgeon initially feeds the desired value R2 and P into the controller as already discussed in context with FIGS. 1 and 2 and the system is operated. Now on the basis of a pressure feedback mechanism the controller determines and creates a desired magnitude of the current which would be needed to be flow through the coil 3 in order to maintain the cavity pressure at the desired value P for a desired outflow rate R2. The Inventors have noticed that if the controller continuously controls the 'electromagnetic devise' 5 the cavity pressure continuously irregularly fluctuates around a preset value and it not at all possible to attain a constant value. Thus the controller is so programmed that once a desired preset tissue cavity pressure is attained and maintained for a certain minimum time interval, for example 10 seconds, the controller would the release the 'electromagnetic devise' 5 from its pressure feedback mechanism and henceforth 'electromagnetic devise' 5 would continue to exert the same uniform force on the piston 2 for indefinite time. The controller is also programmed that if the cavity pressure either decreases or increases by a certain minimum magnitude and for a certain minimum time, the controller would again bring the 'electromagnetic devise' 5 under its influence and the current passing through the coil 3 is suitably varied such that the desired cavity pressure P is again achieved and once this newly established desired cavity pressure P is maintained for a certain minimum time the 'electromagnetic devise' is again released from the influence of the controller 14, and such sequence of events can go on for indefinite time. This implies that in an endoscopic procedure the 'electromagnetic devise' operates independently, that is without the influence of the controller, for most of the surgical time. Hypothetically, it may be assumed that in an endoscopic procedure the 'electromagnetic devise' would be under the influence of the controller for only a very minimal time, say 5% of the total surgical time. As discussed in this paragraph one of the reasons for the cavity pressure to fall below the desired value could be fluid intravasation through the tissue walls. At this point it is also thought essential to state that so long as a constant current is flowing through the coil 3 the total force exerted on the piston 2 by the magnet 4 also remains constant thus the rate R1 at which fluid escapes from the container 1 into the inflow tube 6 also remains constant. A major part of the fluid related to R1 flows into the cavity 9 while the some fluid escapes via the constriction site 29.

Till date the surgeons were left with only two options, either to ignore the tissue cavity pressure variations by not correcting them, or to externally and actively correct such pressure variations. To externally and actively correct the variations in the cavity pressure, a controller was incorporated and the working of the pumps was essentially controlled by a controller. Incorporation of the controller controlling the operation of the pumps did not provide any benefit. The controllers used to initiate the controlling action only after the variations in the cavity pressure had subdued. Thus, the controlling action initiated by the controller instead of benefiting the surgeon leads to an undesirable turbulence inside the cavity and also tends to amplify the resultant movement excursions of the tissue cavity walls.

The Inventors believe that the controller provides proper corrective action (by continuously controlling the operations of the pumps) only if the fluctuations in the cavity pressure are gradual and are not highly instantaneous. Thus implying that the controller would be able to provide proper corrective action only if the quantitative rise or fall in the cavity pressure is over a minimal substantial time period. As the time period to detect variation in the cavity pressure and commence corrective action is ideally in the range of 2 to 4 seconds, if the quantitative rise or fall in the cavity pressure is over very short time period, the suggested mechanism of providing a controller will be unsuitable. Under such instances, instead of providing any corrective action, the controller destabilizes the system and induces additional pressure fluctuations inside the cavity (because of commencing a corrective action at a delayed stage). Thus it takes substantial time for the system to once again get stabilized.

The Inventors have surprisingly found that by incorporating a housing tube 28 provided with a constriction site 29 inherently and passively corrects the pressure variations due to physiological tissue cavity wall contractions and the mechanical movement of the tubes and the endoscope, which ultimately translates in limiting the variations in the size of the cavity. The Applicants would like to highlight that it is important to control both the variations in the pressure inside the cavity and the changes in the size of the distended cavity. Large variations in the pressure inside the cavity or in the size of the cavity are detrimental to an endoscopic surgical procedure. In all the prior art systems attempts were made to either control the variations in the pressure or the variations in the cavity size. But none of the prior art document the need to control both the cavity pressure variations and the cavity size variations and hence failed to provide a safe and ideal system. During the contraction of the cavity, a minute quantity of the fluid is pushed out of the cavity. If during this stage the system does not provide a way for releasing the fluid being pushed out, it leads to an undesirable transient increase in the cavity pressure. A similar explanation can be proposed for a cavity wall expansion which would require some adequate fluid to be instilled into the cavity during the cavity expansion phase. The incorporation of the housing tube having the constriction site in the present system controls both the variations in the pressure inside the cavity and the changes in the size of the distended cavity. If the cavity contracts some fluid escapes via the constriction site 29 in the direction of point 30. Similarly if the tissue cavity expands a suitable volume of fluid is sucked into the cavity from the irrigation circuit such as from point 19 which is associated with a transient decrease in the rate at which fluid escapes via the constriction site 29. Thus the housing tube having the constriction site avoids the instantaneous pressure surge inside the cavity which is harmful to the patient. The size of the diameter at the constriction automatically controls the amount of fluid passing through the housing tube, thereby controlling the amount of fluid being pushed out of the cavity or being sucked into the cavity. Inclusion of the housing tube with the constriction site therefore minimizes the instantaneous variations in the size of the distended cavity.

As already discussed the only reason for operating the 'electromagnetic devise' 5 independent of the pressure feedback mechanism is to avoid unnecessary corrections of minor pressure variations caused by physiological cavity wall contractions and the mechanical movements of the irrigation tubes. The concept of physiological cavity wall contractions has been explained in detail under the heading 'basic physics of cavity distension'. In the present invention the physiological variations in cavity pressure are automatically corrected by the constriction site 29 without the need of a controller. If the cavity contracts a minute quantity of fluid which is pushed out of the cavity and this causes a corresponding volume of fluid to escape vie the constriction site 29. It is to be noted that one end of tube 28 opens at atmospheric pressure via opening 30 thus fluid escapes via the constriction site 29 against a zero pressure head, which is atmospheric pressure. Thus, the transient, insignificant and instantaneous rise or fall in cavity pressure variations get stabilized at a desired preset value within a fraction of seconds. Alternatively if the cavity expands a suitable volume of fluid is sucked into the cavity from the inflow circuit such as point 19 and this is accompanied by a corresponding transient decrease in the flow rate at which fluid is escaping via the constriction site 29 but if the magnitude of the said physiological expansion is more fluid may even be sucked into the cavity via the constriction site 29. This implies that the constriction site 29 is helping in maintaining a stable cavity pressure despite physiological cavity wall contractions by suitably varying the magnitude of an imaginary fluid flow vector passing through the constriction site 29. Normally the direction of such imaginary vector is always towards the open distal end 30 of tube 28 while its magnitude constantly varies to take care of the pressure changes resulting due to physiological cavity contractions. However if the cavity expands physiologically by an excessive magnitude the direction of the said imaginary vector could even be reversed, that is fluid could even be sucked into the cavity via the constriction site 29. Normally a cavity continuously contracts and dilates by approximately the same magnitudes thus there is little logic to check the minor pressure variations emanating from the said contractions. Also the opening of the constriction site 29 does not allow the said physiological cavity pressure fluctuations to cause any significant cavity wall movement excursions by allowing to and fro movement of fluid flow through its lumen. However, if the said pressure changes are made to be corrected by a controller, as is done in the prior art systems, the cavity wall may exhibit significant irregular pressure fluctuations which may result in significant movement excursions of the cavity wall, thus disallowing a predictably stable mechanical stabilization of the cavity walls. However, in the eventuality of fluid intravasation the fall in cavity pressure drop is relatively more permanent in nature thus needs to be corrected by the controller. As already explained the controller is so programmed that the inflow pump 'electromagnetic devise' 5 automatically comes under the pressure feedback control mechanism of the controller in case the cavity pressure changes by a desired minimum preset magnitude and for a desired preset time interval. As a safety precaution a provision can be made in the controller via suitable input means to fix an upper safe limit for the cavity pressure P so that this safe limit is not exceeded accidentally.

Figure 6:
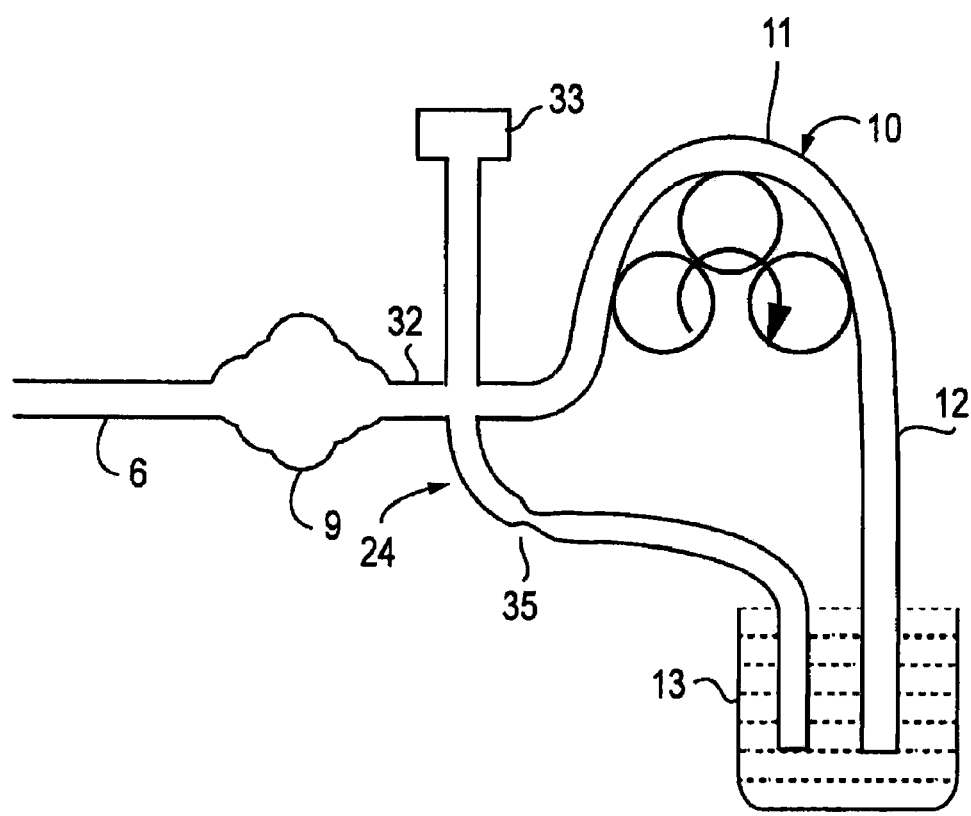
FIG. 6 shows the tissue cavity, the outflow pump along with an optional pressure transducer and an optional constriction site housing tube on the outflow.

Referring to FIG. 6 a constriction site housing tube similar to tube 28 labeled as 34 can be attached to the outflow tube 32 as shown in FIG. 6. In the said tube 34 the said constriction site is labeled as 35. Such tube can serve a number of purposes. Tube 34 can be utilized for relatively faster evacuation of air bubbles from the cavity. The said bubbles are invariably created inside the cavity as a result of electrosurgical cutting and coagulation or they may enter the cavity while the endoscope is being introduced into the cavity. Such bubbles cause extreme nuisance for the surgeon because they obscure vision and thus the surgical time may be greatly increased. In routine surgery the surgeon moves the tip of the resectoscope near the bubble and the bubble is sucked out of the cavity by the process of continuous flow irrigation. However in certain situations it may not be possible to bring the tip of the resectoscope near the bubble, one such situation is when bubbles accumulate inside a very deep cornuae associated with a long septum, the diameter of the cornuae being less than the outer diameter of the resectoscope. In such a situation the tubal opening situated at the center of the cornuae can only be visualized after evacuating such bubbles from the cavity. In such situation the bubbles can be quickly evacuated without moving the tip of the resectoscope near the bubbles by simply opening the constriction 35 in the tube 34. However such maneuver tends to completely collapse the cavity. Thus if the resctoscope tip is only moderately away from the bubbles the constriction site 35 is opened only partially so that the bubbles are sucked out and the cavity collapses by a relatively smaller magnitude. In place of the adjustable constriction site 35 a pressure release safety valve may be incorporated as a safety feature, however it is more beneficial to install such pressure safety valve in the inflow circuit. The tube 34 may also be used for quickly flushing air bubbles from the irrigation tubes by fully opening the constriction site 35 for a few seconds. The tube 34 may also be used for any other purpose as deemed fit by the surgeon. However the said tube 34 has intentionally not been included in the other diagrams because by including the tube 31 in the other block diagrams it would have become very difficult to explain the basic physical principals of the invention. However tube 34 is a very beneficial component and is thus recommended to be incorporated in the system of the proposed invention. The opening and closing of the constriction site 35 can also be regulated manually to help in various special advanced endoscopic applications. Incorporation of tube 34 with the variable constriction site 35 can help in reducing the substantially high amplitude pressure variations inside the cavity caused by abnormally large cavity wall contractions, but such phenomenon is only rarely encountered. The tube 34 instead of directly emptying into the container 13 may also be connected to tube 12. Also an additional pressure transducer 33, as shown in FIG. 6, may also be attached on the out flow tube 32, if desired, as shown in FIG. 6. However the said pressure transducer 33 has intentionally not been included in the other diagrams of the invention because by doing so it would have become very difficult to explain the basic physical principals of the invention.

Also in context with FIGS. 1 to 5 the pressure sensed by the pressure transducer 7 is almost equal or slightly higher than the pressure inside the tissue cavity 9, as it simulates a static system.

Cavity Pressure or the Outflow Rate, Both can be Altered Independently without Varying the Value of the Other Parameter Referring again to FIG. 3 an hypothetical endoscopic procedure is being considered wherein surgery is being performed at an outflow rate R2, the constriction 29 diameter having been fixed at some value D and a resultant cavity pressure P being created and maintained. In such a hypothetical situation as long as R2 is not altered the cavity pressure P would remain predictably constant throughout surgery resulting in a predictably stable mechanical distension of the tissue cavity walls which culminates in constant clear visualization throughout the endoscopic procedure. If in the said hypothetical procedure the cavity pressure needs to be increased without altering the out flow rate R2 then a new higher pressure value is fed into the controller and the controller determines and establishes the magnitude of the increased current passing through the coil 3 such that the desired higher cavity pressure is achieved and maintained. Similarly if the cavity pressure needs to be decreased without altering the out flow rate R2 then the value of the desired lower pressure is fed into the controller and the controller determines and establishes the magnitude of the decreased current passing through the coil 3 such that the desired lower cavity pressure is achieved and maintained. In the said hypothetical endoscopic procedure if the outflow rate R2 needs to be increased without altering the cavity pressure P then the value of the increased R2 is fed into the controller and the controller automatically determines and establishes the magnitude of the decreased current passing through the coil 3 such that the cavity pressure is maintained at the same desired pressure value P. In a similar manner the outflow rate R2 can also be decreased without altering the cavity pressure.

Selection of a Suitable Diameter for the Constriction Site

The most suitable diameter D for the constriction site 8 can be selected for an endoscopic procedure or procedures but such an approach must take into consideration the operational efficiency needs in context with the cavity pressure fluctuations which might occur due to the inevitable physiological contraction or expansion of the cavity walls. If the diameter of the constriction site 29 is very small then the said transient pressure fluctuation in the cavity pressure would be of a relatively larger magnitude and would last for a relatively longer time interval but the associated resultant movement excursion of the cavity wall would be of a relatively small amplitude. Similarly if the diameter of the constriction site 8 is relatively large then the said transient cavity pressure fluctuations would be of a relatively smaller magnitude and would also last for a relatively shorter time interval but the associated resultant movement excursion of the cavity walls would be of a much larger amplitude. These statements are explained by the help of three hypothetical numerical assumptions as stated in table 1 which is as follows:

been added and the nature and function of all these items has already been explained in the preceding sections of the manuscript.

Determination of Instantaneous Real Time Rate of Fluid Intravasation

The instantaneous rate at which the irrigation fluid enters into the patient's body via the walls of the tissue cavity 9 is termed as the instantaneous real time rate of fluid intravasation and is being termed as R3. Now R3 is obviously depends upon the magnitude of current flowing through the coil 3, P and R2. Thus R3 can be determined by a suitable mathematical expression containing P, R2 and the current magnitude.

An Alternative Embodiment of the Invention

In context with the system shown in FIG. 3 it is also possible to have a system in which the cavity pressure is maintained and regulated by continuously varying the diameter D at the constriction site 29 by a pressure feedback mechanism utilizing a controller. The diameter D at the constriction site 29 could also be intermittently regulated by a controller as and when required for example in the eventuality of fluid intravasation or extravasation thus implying that the diameter D shall be free from the influence of the controller for most of the time and shall be brought under the influence of the controller only when needed and that also for only a small part of the total surgical time. In the 'variable constric-

TABLE 1

| Serial number of the assumption | A hypothetically assumed numerical value of the constriction site diameter | A hypothetically assumed numerical value of the magnitude of a transient pressure surge associated with a physiological cavity wall contraction movement | A hypothetically assumed time interval for which the said pressure surge exists | A hypothetically assumed magnitude of the associated resultant cavity wall movement excursion |
|---|---|---|---|---|
| 1 | 0.05 mm | 20 mm Hg | 3 seconds | 0.5 mm |
| 2 | 0.1 mm | 5 mm Hg | 1 second | 1 mm |
| 3 | 0.9 mm | 1 mm Hg | 0.5 seconds | 5 mm Hg |

(Note: A similar table can be hypothetically constructed taking into consideration cavity wall expansion, instead of contraction.)

In context with routine endoscopic procedures the above mentioned hypothetical situation associated with serial number 2 is most acceptable out of the three hypothetical examples because a high magnitude cavity wall movement excursion is not at all desirable while a moderately high transient pressure surge may be acceptable in most endoscopic procedures. Thus the nuisance value of a cavity wall movement excursion is relatively more than the nuisance value of the said transient pressure surge. However the amplitude of the pressure surge should also be not very high because it may lead to intravasation and other problems.

Thus while selecting the diameter of the constriction site two things are kept in mind, the operational needs of the endoscopic procedure and the anticipated cavity wall contraction and expansion movements. Thus in those endoscopic procedures where mechanical stability of the cavity walls is important the numerical value of the constriction site diameter D should be relatively small. There may be endoscopic procedures where mechanical stability of the cavity walls is not the major concern and in such case a relatively higher value of D may be chosen.

Figure 4:
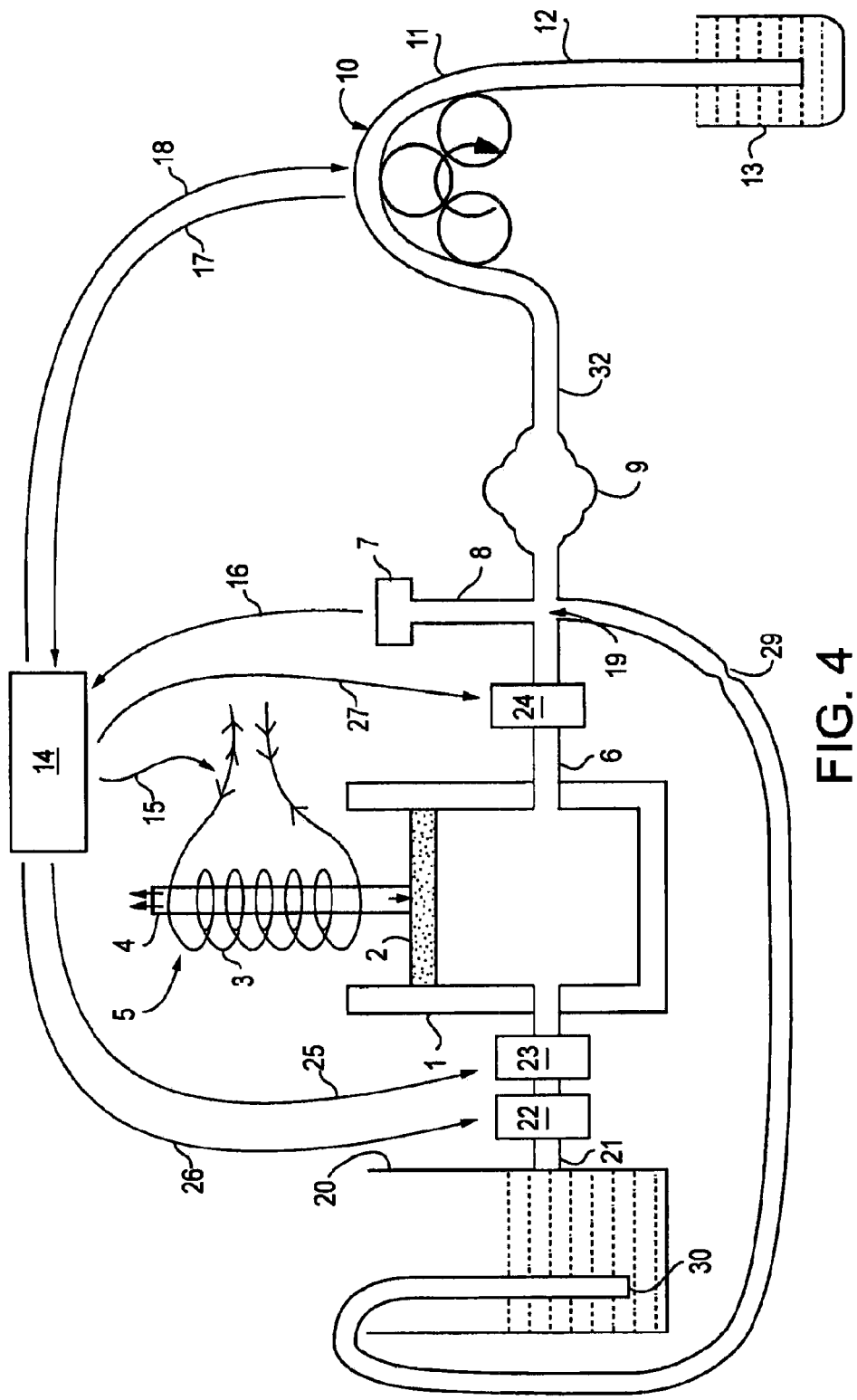
FIG. 4 is similar to FIG. 2 except that a constriction site housing tube 28 has been included.
Figure 5:
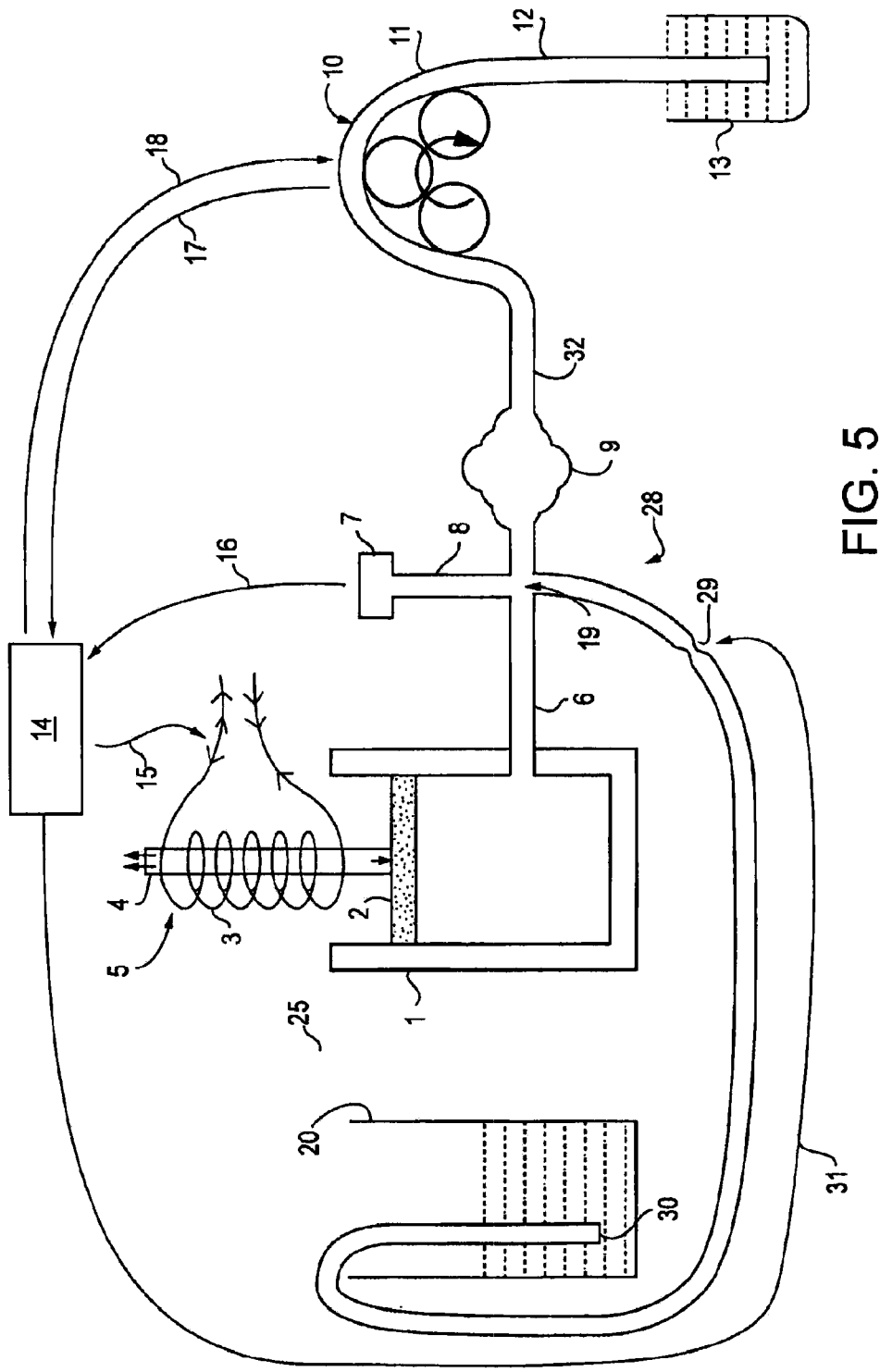
FIG. 5 is similar to FIG. 3 except that the constriction site 29 has been shown to be under the influence of the controller.

FIG. 4 is the same as FIG. 3 except that a fluid supply tube 21, a pump 22 and flow controlling valves 23 and 24 have tion' system proposed in this paragraph a current having a constant magnitude would constantly flow through the coil 3 and the outflow pump would also operate at a desired fixed flow rate R2 and the cavity pressure would be regulated only by varying the diameter D at the constriction site 29. At the start of the surgery outflow rate and the desired cavity pressure P would be set by feeding suitable related values into the controller after which the controller would not influence or regulate the 'electromagnetic devise' 5 and the outflow pump 10 and the cavity pressure would be maintained only by varying the diameter D at the constriction site 29. In order to vary the diameter at the constriction site 29 a suitable devise like the 'electromagnetic devise' 5 could be installed over the housing tube 28 at the constriction site 29. Such a devise is not a devise which would either totally close or totally open the lumen of the pipe. By the help of the said devise the lumen diameter would be varied in a controlled manner and not just by totally opening or totally closing the lumen. Such a devise would control the diameter D at the constriction site 29 by a pressure feedback mechanism. In context with the present paragraph the controller shall regulate the amount of electrical energy supplied to the coil of the said 'electromagnetic devise' such that the magnetic rod presses over the constriction site 29 with an adequate force which would in turn adequately vary the overall size of the inner lumen of the tube 28 at the site of the constriction site 29. Thus the inner diameter of the tube shall be a function of the magnitude of the current passing through the coil of the said 'electromagnetic devise' devise.

Figure 7:
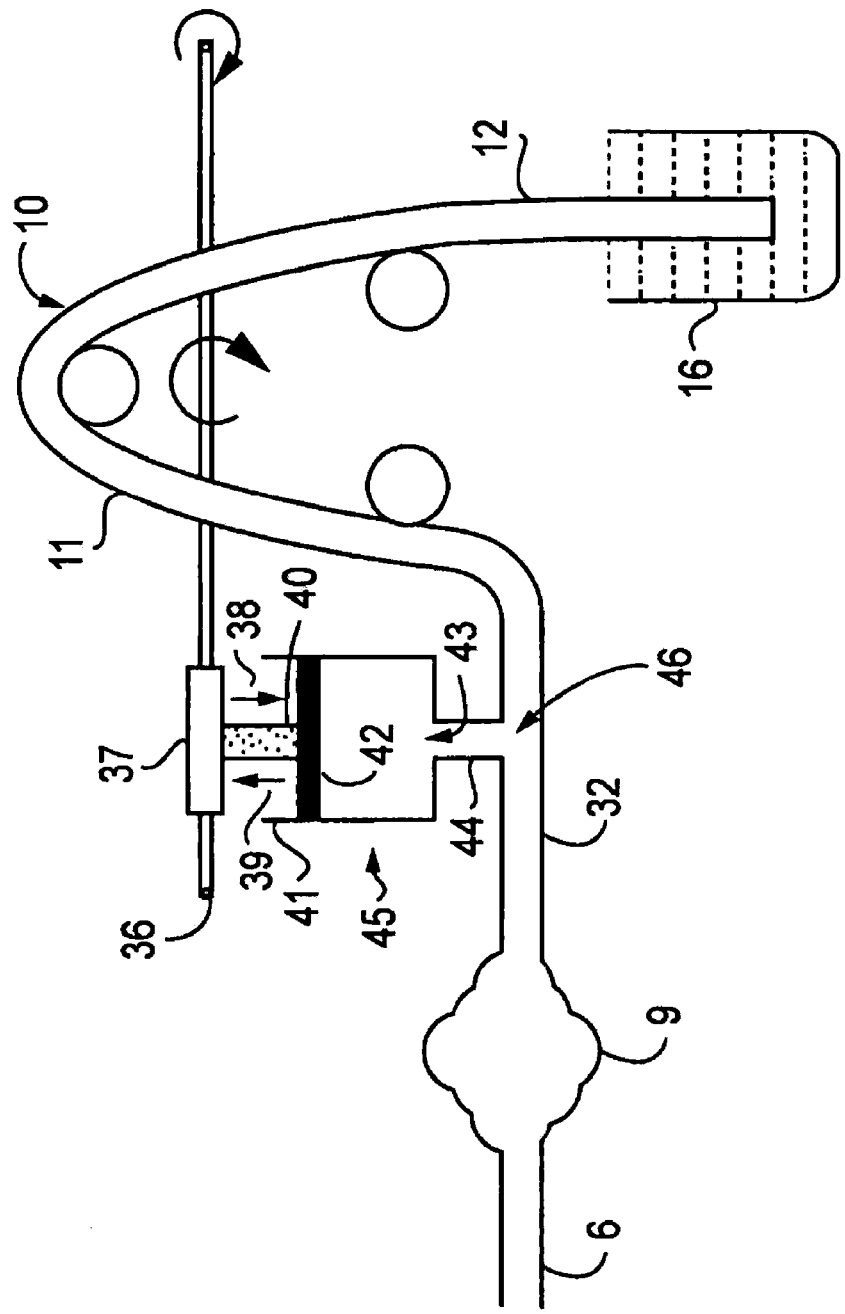
FIG. 7 shows the 'pressure pulse dampening system' synchronized with the outflow pump.

A Method to Dampen the Pressure Pulsations Caused by the Outflow Positive Displacement Pump Referring to FIGS. 1 to 6 the outflow positive displacement pump, that is the outflow peristaltic pump 10 creates pressure pulsations which are invariably transmitted to tissue cavity 9 in a retrograde manner thus leading an undesirable turbulence inside the tissue cavity. Thus a system of dampening, that is reducing the said pressure pulsations caused by the outflow positive displacement pump 10 is being proposed in FIG. 7. FIG. 7 shows a 'pressure pulse dampening system' 45. Referring to FIG. 7 the fluid pressure, such as at a point 46, is pulsatile in nature because the peristaltic pump 10 constantly extracts fluid from the tissue cavity via the outflow tube 32 in a pulsed manner and not in a continuous manner and this leads to fluid pressure pulsations. The said pulsations are transmitted to the tissue cavity 9 in a retrograde manner via the outflow tube 32. Hypothetically assuming that the pump 10 rotates at fixed RPM then in that case the frequency of such pulsations would remain uniformly the same all through the operation of the pump. If a graph is plotted for the said pulsations, by relating the fluid pressure to the 'Y' axis and the time to the 'X' axis, then such graph would have a uniform shape having positive and negative pressure swings of a predictably fixed amplitude and fixed frequency. It is to be noted that as the pump RPM is increased the frequency as well as the amplitude of the said pressure swings also increase. The said pulsations are produced because each time any one roller of the peristaltic pump comes in apposition with a fixed point, for example the inlet end of the peristaltic pump 10, some fluid is withdrawn from the outflow tube 32 by the outflow peristaltic pump via its inlet end in the form of a bolus. The wave form of such resultant pulsations need not be sinusoidal, but for the sake of an easier understanding let the said waveform be hypothetically assumed to be sinusoidal in nature. As already stated, if the pump RPM increases then along with the frequency the amplitude of the said waveform also increases. When the pump 10 rotates in the direction of the curved arrow fluid is extracted from the outflow tube 32, the cavity 9 and the inflow tube 6 and let all three of these collectively be termed as 'fluid extraction region'. In physical terms the said pressure pulsations are produced because the fluid tends to be extracted from the 'fluid extraction region' in the form of regular pulses wherein each pulse corresponds to a fixed volume of fluid pulled by a roller from the 'fluid extraction region' in the form of a bolus of fluid. Thus the motion of each roller would correspond to one complete sinusoidal pressure wave. Thus the motion of each roller would correspond to one complete sinusoidal pressure wave, having assumed the said waveform to be sinusoidal as previously stated. The movement of a single roller in relation to a fixed point such as the inlet end of the pump can be hypothetically divided into three parts, that is, part one when the roller approaches the said point, part 2 when the roller is in apposition with the said point and part 3 when the roller moves away from the said point. Let the parts 1, 2 and 3 be collectively termed as 'single roller movement' and the time taken to accomplish the said 'single roller movement' be termed as 'single roller time'. Assuming the pressure waveform to be a sinusoidal curve, each 'single roller movement' corresponds to one complete sinusoidal pressure waveform consisting of a positive pressure pulse followed by a negative pressure pulse or vice versa. Also the time period of the assumed sinusoidal wave form would be equal to 'single roller time'. If during a negative pressure pulse an adequate volume of fluid is removed from the 'fluid extraction region' and during a positive pressure pulse the same adequate volume of fluid is again added back into the 'fluid extraction region' the sinusoidal nature of the pressure waveform could get dampened and the resultant waveform would get transformed into an almost straight line curve. The resultant waveform could theoretically be an absolute straight line if the wave form associated with the said process of adding and removing adequate volumes of fluid from the 'fluid extraction region' absolutely resembled with the wave produced as a result of the pulsatile flow of the peristaltic pump and the phase difference between the two waves was exactly 180 degrees however this may not be achieved in practical situations. However a substantial dampening of the resultant waveform could be practically achieved if a syringe system was synchronously coupled with the outflow peristaltic pump 10 and the single outlet end of the said syringe system was connected with the 'fluid extraction region'.

The said syringe system is shown in FIG. 7. The syringe system 45 consists of a piston 42 denoted by a shaded area and the piston 42 moves up and down inside a cylinder 41 while making a watertight contact with the inner walls of this cylinder 41. One end of a straight rod 40 is connected to the piston while the other end of this rod 40 is connected to a coupling mechanism 37 housed on a common rotating shaft 36. The coupling mechanism 36 and the peristaltic pump 10, both are attached on this common shaft 36. The coupling mechanism 37 is so designed that it converts the rotary motion of the shaft 36 into a linear up down motion of rod 40 which is ultimately manifested as an up down movement of piston 42 inside the cylinder 41. The up down motion of the rod 40 is denoted by arrows 38 and 39. Thus the shaft 36 is a common shaft which mechanically operates both, pump 10 as well as the syringe system 45. The direction of rotation of the shaft 36 is denoted by a curved arrow located at the right end of the shaft 36. The syringe system 45, as the name suggests, resembles a hypodermic syringe used for giving injections to patients. Obviously, the syringe system 45 has only one single opening 43. A tube 44 extending between the opening 43 and the outflow tube 32 connects the syringe system to the outflow tube 32. Tube 32 is a part of the said 'fluid extraction region' described in the previous paragraph. Thus the syringe system can be considered to be connected with the said 'fluid extraction region'. The opening 43 can be referred to as an 'outlet end' or an 'inlet end' because the syringe system can push as well as pull fluid from the 'fluid extraction region'. However for the sake of convenience henceforth the opening 43 shall be termed as the outlet end of the syringe system 45. The coupling mechanism 37 is so designed that the vertical movements of the syringe system can be accurately synchronized with the rotary motion of the peristaltic pump 10. The piston 42 can move up>down>up or down>up>down, depending upon the initial position of the piston at the start of the motion and let each such movement of the piston be termed as a 'complete piston movement'. The coupling mechanism 37 is so designed that while the peristaltic pump 10 rotates by 360 degrees the syringe system correspondingly exhibits 'complete piston movements' which are equal to the number of the rollers of the peristaltic pump. Thus for a peristaltic pump which has three rollers then for each 360 degrees rotation of the peristaltic pump the syringe system exhibits three 'complete piston movements' while for a peristaltic pump with four rollers four 'complete piston movements' would occur for each 360 degree rotation of the peristaltic pump. The syringe system is synchronized with the peristaltic pump via the coupling mechanism 37 in such manner that while a roller of the peristaltic pump produces a negative pressure pulse the syringe system pushes fluid into the 'fluid accumulation region' and while the same roller produces a positive pressure pulse the syringe system pulls out an equivalent volume of fluid from the 'fluid accumulation region'. In order to dampen the pulsations of the peristaltic pump, besides mechanically synchronizing the syringe system with the peristaltic pump, the volume of fluid pulled in or pushed out of the syringe system corresponding to each upward or downward movement of the piston also has to be accurately adjusted, and the same may be done manually by a 'hit and try method'. The volume of fluid pulled in or pushed out by the syringe system depends upon the linear movement excursion of the piston 42. Also the magnitude of the downward piston excursion is equal to the magnitude of the upward piston excursion, thus the volume of fluid pushed out is always equal to the volume of fluid pulled in during each downward or upward movement. Thus the coupling mechanism 37 has two functions, synchronization of the syringe system with the peristaltic pump and adjusting the volume of fluid pulled in or pushed out by the syringe system for each upward or downward movement of the piston. The synchronization and the determination of the said volume to be pushed out or pulled into the syringe system are done manually such that a substantial dampening of the pressure pulsations is achieved and once this is achieved the synchronization at the level of the coupling 37 is never again disturbed and the volume of fluid pulled in or pushed out of the syringe system for each movement excursion is also not changed thereafter. After the coupling 37 is adjusted with respect to synchronization and the volume of fluid to be pulled in and pushed out, the peristaltic pump pulsations shall continue to remain dampened independent of the peristaltic pump RPM and the nature of rotation, that is fixed or variable RPM. In simpler terms the peristaltic pump pulsations would continue to remain dampened even at a high pump RPM. Also the point at which the syringe system 45 is connected to the said 'fluid extraction region', for example the outflow tube 32, then the position of such a point should also not be changed thereafter because this may bring about a phase difference between the waveform related to the peristaltic pump pulsations and the waveform related to the syringe system pulsations, thus the resultant dampening could no longer be satisfactory. Also preferably the outlet tube 44 of the syringe system should be connected as close to the outlet end of the inflow peristaltic pump as possible.

Figure 8:
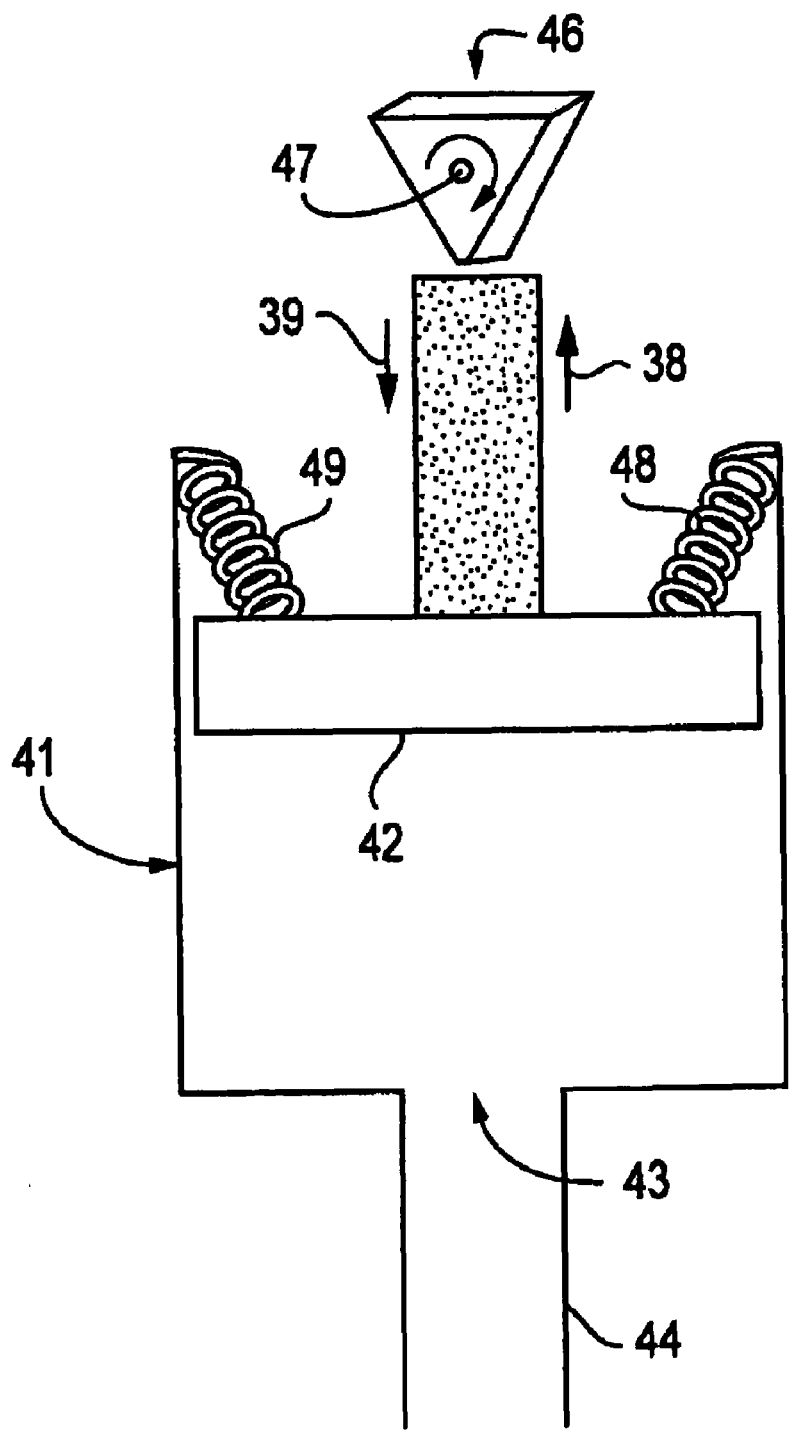
FIG. 8 shows a detailed layout of the 'pressure pulse dampening system' along with a coupling means.

The coupling 37 can be compared to some extent with the conventional CAM system present in automobile engines. Any specific mechanical design for the coupling 37 is not important, it is the resultant function of the coupling 37 with respect to the piston movement, as already described, which is important. The coupling 37 can have many mechanical designs. FIG. 8 shows one such possible mechanical design for the coupling 37. In FIG. 8 a small length of the common shaft 36, which is related to the coupling 37, has been made of triangular shape as seen in its cross sectional view and the same is labeled as 46. Let this triangular part 46 be termed as the 'piston coupler'. The edges of the piston coupler are shown sharp however they could preferably be rounded to suit various operational needs. Similarly the size of the 'piston coupler' could also be increased or decreased in order to decrease or increase the volume of fluid displaced by the cylinder during a downward or upward movement of the piston. The central axis point of the 'piston coupler' is denoted by point 47. In case the dimensions of the 'piston coupler' are chosen to be relatively larger than the dimension of the common shaft 36, the point 47 could also represent the point at which the common shaft 36 passes through the 'piston coupler' and in such a situation the 'piston coupler' 46 could be manually rotated on the common shaft 36 in a clockwise or anti clockwise direction and then locked mechanically at a position which provides the most accurate synchronization. The springs 48 and 49 extending between the inner walls of the cylinder and the piston exert a constant and substantially large upward pull on the piston 42 which causes the rod 40 to constantly be in apposition with the 'piston coupler' 46. The springs can be one or more than one in number and the springs can also be substituted by any other mechanical means also which provide an active upward movement of the piston. The 'piston coupler' 46 is assumed to be able to apply a substantially large downward force on the piston 42 via rod 40 such that a corresponding transient negative fluid pressure inside the cylinder can be totally neglected in the face of the said large substantial downward force. In a similar context, the springs 48 and 49 are capable of pulling up the piston with a substantially large force such that a corresponding transient positive fluid pressure pulse inside the cylinder could be totally neglected. The idea is that the downward movement of the piston should not be aided by a transient corresponding negative pressure pulse inside the cylinder, this downward movement should be an active movement for which energy is to be derived from the shaft 26. Similarly the upward movement of the piston should not be aided by a corresponding transient positive pressure pulse inside the cylinder, this upward movement should be an active movement for which energy is to be derived from the springs 48 and 49. The energy for the said upward movement of the piston could also be derived from the shaft 36 if suitable mechanical provision facilitating an active upward movement of the piston could be provided at the level of the coupling 46.

It is important to note that it is not mandatory to use the said 'pressure pulse dampening system' with a peristaltic pump only as, with suitable mechanical modifications, the 'pressure pulse dampening system' could be used beneficially with any type of a positive displacement pump.

The 'pressure pulse dampening system' could also be a mechanism like the 'piston coupler' shown in FIG. 7 whose rounded edges could directly impinge on a suitable area situated on the outer surface of the 'fluid extraction region' in a uniform synchronized manner, as described, such that this results in continuous uniform synchronized variations in the total volume capacity of 'fluid extraction region'. The said suitable area on the outer surface of the 'fluid extraction region' could be a membrane made consisting of a strong resilient polymeric material having an adequate elasticity. The said membrane should also be sufficiently thick and should have an adequate elasticity such that an outward movement of such membrane, a movement related to the upward pull by the said springs, applied a substantially larger force in comparison to force related with the transient corresponding pressure pulse.

A System of Incorporating Multiple Peristaltic Pump Tubes

In the preceding parts of the manuscript the peristaltic pump 10 is shown to have one single tube 11 which come in contact with the rollers of the peristaltic pumps. Arbitrarily referring to the outflow pump 10, $$R2 = \frac{\pi \times B^2 \times L}{4} \times \text{RPM} \text{ where } R2 = \text{Flow rate of pump 14,}$$

B=inner diameter of the peristaltic pump tube 4, L=length of peristaltic pump tubing tube 11 and RPM=revolution per minute of pump 5. If the value B is doubled then for the same RPM the flow rate R1 doubles. Similarly if L doubles then also for RPM the flow rate R2 doubles. However keeping in mind the mechanical constraints the values B and L cannot exceed a certain practical value. However if two tubes like tube 11 are used in parallel in the pump 14 then the mathematical expression for the flow rate could be written as follows:

$$R2 = \frac{\pi \times B^2 \times L}{4} \times \text{RPM} \times 2$$

This implies that if two peristaltic pump tubes are used instead of one single tube then the flow rate becomes double for the same RPM and if three tubes are used then the flow rate becomes three times and so on. The frequency of the 'pressure pulsations' created by a peristaltic pump is directly proportional to the pump RPM. The said 'pressure pulsations' are undesirable thus it is helpful to keep their frequency as minimal as possible if the flow rate is not compromised. Thus this system of incorporating two or more peristaltic pump tubes helps in attaining a higher flow rate for a relatively lesser RPM. It is but obvious that the said two or more than two parallel tubes are connected to each other at the inlet and the outlet ends of the peristaltic pump.

Determination of the Instantaneous Real Time Rate of Fluid Intravasation

Fluid intravasation is a process by which the irrigation fluid enters into the patient's body system and if excess volume of fluid is intravasated it can be dangerous to the patient's life. Thus, keeping in mind surgical safety, it is extremely important to constantly know the rate at which such intravasation occurs so that corrective surgical measures can be taken before a dangerous volume of fluid intravasates. The inventors propose that one fluid flow rate sensor each be incorporated in the inflow tube and the outflow tube. Referring to FIG. 3 the inflow flow rate sensor should be located in the inflow tube 6 anywhere between the inlet port of the endoscope and the point at which the distal end of the constriction site housing tube 28 is connected to the inflow tube 6 as at point 19. However in context with FIGS. 1 and 2 such a fluid flow rate sensor would be placed anywhere in the tube 6. Such a flow rate sensor would measure the rate at which fluid enters into the tissue cavity 9 and the same is being termed as 'cavity inflow rate'. Obviously the 'cavity inflow rate' is the true inflow rate for the tissue cavity. Similarly the outflow flow rate sensor should be located anywhere in the out flow tube between the outflow port of the endoscope and the inlet end of the outflow peristaltic pump 10 or any other outflow positive displacement pump. However if an additional or optional constriction site housing tube 34 is also connected to the out flow tube 32 as shown in FIG. 6 then the outflow flow rate sensor should be located between the outflow port of the endoscope and the point at which the proximal end of the constriction site housing tube 34 is connected to the outflow tube 32. The outflow flow rate sensor measures the rate at which fluid is extracted from the tissue cavity which is the same as R2 that is the flow rate of the outflow pump. Now the real time rate of fluid intravasation, being termed as R3, can be determining by subtracting R2 from the 'cavity inflow rate', the mathematical expression for the same being can be written as R3=Cavity inflow rate−R2. The said flow rate sensors should be accurate, reliable, easy to install and should not have any movable parts. The inventors suggest that a the said sensor comprise of a heating coil in physical contact with a metal plate for heating the same and a temperature sensor placed in contact with the metal plate, the temperature of the metal plate being a function of the fluid flow rate. The said flow rate sensors are electrically connected with a microcontroller which automatically subtracts R2 from the 'cavity inflow rate' to give the value R3. The value R3 can also be further integrated with respect to time to give the total volume of fluid intravasated over a certain time interval. The said temperature related flow rate sensor could be a 'hot wire anemometer'.

Determination of the Real Time Rate of Fluid Intravasation without Using Fluid Flow Rate Sensors Referring to FIG. 1 the tissue cavity pressure P is a function of the current in amperes passing through the coil 3, the cavity outflow rate (R2) and the real time rate of intravasation (R3). The value P increases as the magnitude of the current in amperes passing through the coil 3 increases and decreases as R3 and R2 increase. Thus a mathematical expression could be derived which contains P, the current in amperes passing through the coil 3, R2 and R3. Such a mathematical expression could be fed into a controller and in this manner the value R3, the real time rate of fluid intravasation could be determined.

The proposed invention has obvious use in hysteroscopic surgery, arthroscopic surgery and TURP surgery. The proposed invention can also be utilized for carrying out endoscopic procedures in the brain and the spine. Brain endoscopic surgery also known as neuro endoscopy is a frequently performed life saving procedure. The human brain has got cavities known as the brain ventricles. Many endoscopic procedures are performed by inserting the endoscope into the brain ventricles and many such procedures utilize continuous flow irrigation. Endoscopic surgery of the spine is also a frequently performed and many endoscopic procedures related to the spine utilize continuous flow irrigation. The proposed invention can be useful in other endoscopic procedures also which require continuous flow irrigation. The present invention can be useful in certain non endoscopic procedures also where a tissue cavity needs to be distended by continuous flow irrigation such as gall stone dissolution, balloon thermal ablation of the endometrium, phako emulsification procedure related to the eye ball cavity and vitrectomy procedure related to the eye ball cavity. The proposed invention can also have useful non medical applications such as reducing fluid turbulence in industrial cavities, such as making fluid pressure absolutely independent of the flow rate in a cavity of industrial relevance.

The advantage of predicting the required volume for the irrigation fluid at the beginning of the surgery has already been explained. Such maneuver though extremely simple is extremely helpful. In the present invention the outflow rate remains fixed all through the surgery unless intentionally changed by the surgeon. The average total surgical time for similar endoscopic procedures usually does no vary and the surgeons on the basic of their past experience always have an idea of the approximate time which an endoscopic procedure takes. Such time multiplied by the chosen outflow rate R2 gives a fairly accurate idea of the total volume of irrigation which would be consumed in the proposed endoscopic procedure if intravasation was to be ignored and the surgeons again by their past experience also have a fairly rough idea of the of the volume of fluid which is intravasated in a certain duration of time for specific endoscopic procedures. In this manner the total fluid that would be required in a particular endoscopic procedure can be roughly evaluated but even such rough evaluation is helpful as explained in a previous paragraph entitled 'Predicting the total volume of required irrigation fluid'. It is advisable to take a slightly greater volume than that predicted by the method described in this paragraph.

The proposed invention can also be used to impart endoscopic training skills by the help of endoscopic experimental models based on the present invention. Also use and scope of the present invention is not limited to human tissue cavities and it may be used for performing multiple endoscopic procedures in animal tissue cavities also and also for imparting training in endoscopic surgeries related to animal tissue cavities.

It is believed that the foregoing description conveys the best understanding of the objects and the advantages of the present invention. It will be understood by those skilled in the art that numerous improvements and modifications may be made to the embodiments of the invention disclosed herein without departing from the departing from the spirit and scope thereof.

The Invention is Unique

There is no other prior art system in which a pump system similar to the inflow pump system of this invention operated via electromagnetic means has been used. Also the concept of 'pressure pulse dampening system' not been described or used in any prior art system. The system of determining the real time rate rate of fluid intravasation by using two hot wire anemometers is also unique.

The Heart and Soul of the Invention

The pump system operated by electro mechanical means is the heart and soul of the invention without which the invention cannot exist.

Advantages of the Proposed Invention

The proposed invention makes endoscopic procedures extremely safe, simple, more accurate and easy to perform. The proposed invention helps the surgeons to perform endoscopic surgeries with greater safety and confidence especially in the initial phase of their learning curve. Also a distending system based on the proposed invention can be used in multiple endoscopic procedures thus reducing the financial burden on the hospital and the patient. The advantages of proposed invention are summarized in the following table 2 along with the corresponding disadvantages of the prior art systems:

TABLE 2

| ADVANTAGES OF THE PRESENT INVENTION: | DISADVANTAGES OF THE PRIOR ART SYSTEMS: |
|---|---|
| It is possible to minimize cavity fluid turbulence to almost negligible levels. | This is not possible in any prior art system. |
| It is possible to create and maintain a desired precise tissue cavity pressure for a desired precise fixed outflow rate including a zero outflow rate. | This is not possible in any prior art system. |
| It is possible to reduce the amplitude of the pressure pulsations created by an outflow positive displacement pump to an almost negligible magnitude irrespective of the pump RPM. | This is not possible in any prior art system. |
| It is possible to reduce the frequency of the pressure pulsations created by an outflow positive displacement pump for the same outflow rate. | Such system is not present in any prior art system. |
| A predictably constant desired fluid pressure can be maintained inside a tissue cavity for indefinite time. | This is not possible in any prior art system. |
| A predictably constant desired fluid pressure can be maintained inside a tissue cavity for indefinite time despite physiological cavity wall contractions. | This is not possible in any prior art system. |
| A predictably constant clear endoscopic visualization is possible. | This is not possible in any prior art system. |
| It is possible to achieve a predictably stable mechanical distension of the cavity walls. | This is not possible in any prior art system. |
| The instantaneous real time rate of fluid intravasation into the patient's body is constantly known by using a hot wire anemometer type of a flow rate sensor. | Such feature is not present in any prior art system. |

CONCLUSION

The proposed invention is novel and unique. The invention relates not only to increasing surgical efficiency in certain endoscopic procedures but it also helps in preventing human morbidity and human mortality in many endoscopic procedures. Thus the proposed invention is extremely useful for entire mankind.

We claim:

1. A system for distending body tissue cavities of subjects by continuous flow irrigation during endoscopic procedures, the system comprising:
an inflow pump comprising a hollow barrel with a proximal open end for holding a non viscous physiologic fluid for continuous flow irrigation during an endoscopic procedure, and a plunger mounted slidably inside the barrel for dispensing the fluid, the plunger being provided with an electromagnetic means for slidably moving the plunger in a to and fro manner inside the barrel so that the plunger is in contact with the fluid, a part of the plunger which is not in contact with the fluid being directly exposed to atmospheric pressure,
wherein the electromagnetic means comprise a coil made of insulated wire being wound around a magnetic rod, the coil being connected to a DC current supplying means of dual polarity,
wherein a partially closed distal end of the hollow barrel of the inflow pump is in direct contact with an inflow tube, the inflow tube dispensing the fluid at a controlled flow rate into the tissue cavity during an endoscopic procedure, to obtain a distended cavity, the flow rate at which the fluid enters into the cavity being termed as the cavity inflow rate, the inflow tube dispensing the fluid at the controlled flow rate directly from the hollow barrel of the inflow pump and directly into the tissue cavity, and only through the inflow tube; and
an outflow port connectable to an inlet end of an outflow pump having an inlet end connected to the tissue cavity through an outflow tube for removing the fluid from the cavity at a controlled flow rate, the flow rate of the outflow pump being termed as the cavity outflow rate, wherein an outlet end of the outflow pump is connected to a waste fluid collecting container through a waste fluid carrying tube.

2. The system as claimed in claim 1, wherein a proximal end of the inflow tube is connected to the outlet port of the hollow barrel and a distal end of the inflow tube being connectable to the inflow port.

3. The system as claimed in claim 1, further comprising an inflow pressure transducer located away from the cavity site, near the outlet port of the hollow barrel, such that the actual pressure inside the cavity is measured.

4. The system as claimed in claim 1, wherein a proximal end of the outflow tube is connected to the outlet port and a distal end of the outflow tube is connected to an inlet end of the outflow pump.

5. The system as claimed in claim 1, wherein the outflow pump is selected from the group consisting of peristaltic pump, piston pump, gear pump and diaphragm pump.

6. The system as claimed in claim 5, wherein the outflow pump is a peristaltic pump.

7. The system as claimed in claim 1, wherein the plunger comprises a piston and the magnetic rod being slidably provided inside the barrel.

8. The system as claimed in claim 1, further comprising a microcontroller electrically coupled to the outflow pump and the electro magnetic means for controlling the cavity inflow and cavity outflow rates.

9. The system as claimed in claim 1, further comprising a tube having a constriction site, a distal end of the same being connected to the inflow tube to provide an exit route for any excess fluid present inside the tissue cavity or being dispensed by the hollow barrel, thereby minimizing turbulence inside the body tissue cavity and maintaining the body tissue cavity pressure at a stable value despite physiological contractions of the body tissue cavity wall.

10. The system as claimed in claim 9, wherein the tube is releasably connected on the inflow tube to enable replacement of the tube with another tube having a different diameter at the constriction site to suit the operational need of the endoscopic procedure.

11. The system as claimed in claim 9, wherein a distal end of the tube is connected to the inflow tube near its proximal end close to the outlet port of the hollow barrel.

12. The system as claimed in claim 9, wherein a proximal end of the tube empties directly into an excess fluid collecting container and is constantly and completely immersed in the container.

13. The system as claimed in claim 9, wherein the tube is provided with a clamping means at the constriction site to enable the user to vary the diameter of the tube at the constriction site to suit the operational needs of endoscopic procedures.

14. The system as claimed in claim 9, wherein the tube is provided with an electromechanical device, to enable the micro-controller to vary the diameter of the constriction site.

15. The system as claimed in claim 9, wherein the diameter of the tube at the constriction site is in the range of 0.001 mm to a maximum value which is less than the overall diameter of the rest of the tube.

16. The system as claimed in claim 9, wherein the diameter of the tube at the constriction site is in the range of 0.01 to 2.5 mm.

17. The system as claimed in claim 1 further comprising a fluid replenishing container connected to the hollow barrel for refilling the barrel.

18. The system as claimed in claim 12, wherein the excess fluid collecting container is connected to the hollow barrel for reusing the fluid collected in the excess fluid collecting container.

19. The system as claimed in claim 17, wherein the fluid replenishing container or the excess fluid collecting container is connected to the hollow barrel by a fluid supply tube.

20. The system as claimed in claim 17, wherein the fluid replenishing container or the excess fluid collecting container is connected to the hollow barrel via a replenishment pump and a fluid supply control valve.

21. The system as claimed in claim 20, wherein an inflow fluid controlling valve is provided on the inflow tube for preventing the fluid from entering into the tissue cavity during fluid replenishment phase.

22. The system as claimed in claim 21, wherein the replenishment pump, the fluid supply control valve and the inflow fluid controlling valve are coupled to the microcontroller.

23. The system as claimed in claim 1, further comprising an outflow pressure transducer connected between a proximal end of the outflow tube and the inlet end of the outflow pump for measuring the pressure in the outflow tube.

24. The system as claimed in claim 23, wherein the outflow pressure transducer is electrically coupled to a microcontroller.

25. The system as claimed in claim 1, further comprising an outflow housing tube having a constriction site being provided between the outflow tube and the waste fluid reservoir.

26. The system as claimed in claim 25, wherein a proximal end of the outflow housing tube is connected to the outflow tube near the inlet of the outflow pump.

27. The system as claimed in claim 25, wherein a distal end of the outflow housing tube is connected to the waste fluid carrying tube or to the waste fluid collecting reservoir.

28. The system as claimed in claim 1, wherein the outflow pump is an outflow peristaltic pump provided with 1 to 5 peristaltic pump tubes connected in parallel between the inflow and the outflow ends of the peristaltic pump for reducing the frequency of pressure pulsation, the tubes being connected to each other at the inflow and the outflow ends of the peristaltic pump and the peristaltic pump tubes rollers of the peristaltic pump.

29. The system as claimed in claim 1, further comprising an outflow pressure pulsation dampening means connected to the outflow tube for dampening the pressure pulsations inside the body tissue cavity caused by the outflow peristaltic pump.

30. The system as claimed in claim 29, wherein the outflow pressure variation dampening means comprises a single outlet syringe mechanism, the piston of the same being coupled synchronously to the outflow pump through a coupling means and the single outlet end of the syringe mechanism being connected to the outflow tube.

31. The system as claimed in claim 1 further comprising a fluid inflow rate sensor connected to the inflow tube.

32. The system as claimed in claim 31, wherein the fluid inflow rate sensor is located in a lumen or wall of the inflow tube for measuring the cavity inflow rate.

33. The system as claimed in claim 31, further comprising a fluid outflow rate sensor connected to the outflow tube.

34. The system as claimed in claim 33, wherein the fluid outflow rate sensor is connected between the proximal end of the outflow tube and the inlet end of the outflow pump for measuring the cavity outflow rate.

35. The system as claimed in claim 33, wherein the fluid outflow rate sensor is located in a lumen or wall of the outflow tube for measuring the cavity outflow rate.

36. The system as claimed in claim 33, wherein the fluid inflow and the outflow rate sensors consist of a heating coil in physical contact with a metal plate for heating the same and a temperature sensor placed in contact with the metal plate for measuring the temperature of the metal plate, the temperature of the metal plate being a function of the fluid flow rate.

37. The system as claimed in claim 36, wherein the fluid inflow rate sensor or the fluid outflow rate sensor is a hot wire anemometer.

38. The system as claimed in claim 33, wherein instantaneous real time rate of fluid intravasation is determined by electrically connecting the inflow and outflow fluid flow rate sensors to a micro-controller.

39. The system as claimed in claim 1, wherein the inflow tube, the outflow tube and the waste fluid carrying tube are flexible, disposable and are made of polymeric material.

40. The system as claimed in claim 3, wherein the inflow pressure transducer is electrically coupled to a microcontroller.

* * * * *